United States Patent
Chen et al.

(10) Patent No.: US 9,664,664 B2
(45) Date of Patent: May 30, 2017

(54) PROBE AND METHOD FOR DETECTING METAL IONS AND CHEMICAL/BIOCHEMICAL MOLECULES

(71) Applicant: Industrial Technology Research Institute, Hsinchu (TW)

(72) Inventors: Cheng-Tai Chen, Zhongli (TW); Pei-Shin Jiang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 161 days.

(21) Appl. No.: 14/582,844

(22) Filed: Dec. 24, 2014

(65) Prior Publication Data
US 2016/0178596 A1   Jun. 23, 2016

(30) Foreign Application Priority Data
Dec. 22, 2014   (TW) .............................. 103144721 A

(51) Int. Cl.
*B82Y 15/00*   (2011.01)
*B82Y 20/00*   (2011.01)
*G01N 33/20*   (2006.01)

(52) U.S. Cl.
CPC ................................... *G01N 33/20* (2013.01)

(58) Field of Classification Search
CPC .................................................. G01N 33/20
See application file for complete search history.

(56) References Cited

U.S. PATENT DOCUMENTS

| | | | |
|---|---|---|---|
| 2005/0074551 A1 | 4/2005 | Huang et al. |
| 2005/0130207 A1 | 6/2005 | Hainfeld et al. |
| 2010/0009845 A1 | 1/2010 | Bonn et al. |
| 2011/0165689 A1 | 7/2011 | Ying et al. |

(Continued)

FOREIGN PATENT DOCUMENTS

| | | |
|---|---|---|
| CN | 101713737 A | 5/2010 |
| CN | 102516997 A | 6/2012 |

(Continued)

OTHER PUBLICATIONS

Park, Ji-Ae, et al. "Gold nanoparticles functionalised by Gd-complex of DTPA-bis (amide) conjugate of glutathione as an MRI contrast agent." Bioorganic & medicinal chemistry letters 18.23 (2008): 6135-6137.*

(Continued)

*Primary Examiner* — Robert Eom
(74) *Attorney, Agent, or Firm* — Birch, Stewart, Kolasch & Birch, LLP

(57) ABSTRACT

A method for detecting metal ions and chemical/biochemical molecules is provided. The method includes providing a probe, wherein the probe includes: a gold nanocluster; a reducing agent and a chelating agent partially capped on a surface of the gold nanocluster, wherein the probe is formed of reducing gold ions by the reducing agent, and the gold ions and the reducing agent have a molar ratio of 1:0.7 to 1:1.9. The probe may interact with several metal ions of an aqueous solution to produce different changes of fluorescent spectra. Chemical/biochemical molecules can be detected by the fluorescent spectra difference caused by the interaction between the metal ions and the chemical/biochemical molecules.

4 Claims, 47 Drawing Sheets

(56) References Cited

U.S. PATENT DOCUMENTS

| 2011/0212090 A1 | 9/2011 | Pedersen et al. |
| 2012/0052513 A1 | 3/2012 | Thalappil et al. |
| 2012/0258126 A1 | 10/2012 | Schøller et al. |
| 2014/0179941 A1 | 6/2014 | Bao |

FOREIGN PATENT DOCUMENTS

| CN | 103115905 A | 5/2013 |
| CN | 103627386 A | 3/2014 |
| TW | 200739074 A | 10/2007 |

OTHER PUBLICATIONS

TW Office Action dated Jun. 2, 2015. pp. 1-4.
Aswathy et al., "Cu2+ modulated BSA-Au nanoclusters: A versatile fluorescence turn-on sensor for dopamine," Microchemical Journal, vol. 116, 2014 (available online May 4, 2014), pp. 151-156.
Cao et al., "Masking method for improving selectivity of gold nanoclusters in fluorescence determination of mercury and copper ions," Biosensors and Bioelectronics, vol. 42, 2013 (available online Nov. 2, 2012), pp. 47-50.
Kang et al., "A cross-reactive sensor array for the fluorescence qualitative analysis of heavy metal ions," Talanta, vol. 129, 2014 (available online Jun. 5, 2014), pp. 296-302.
Li, "Fluorescence-Enhanced Sensing Mechanism of BSA-Protected Small Gold-Nanoclusters to Silver(I) Ions in Aqueous Solutions," The Journal of Physical Chemistry, vol. 117, Jul. 10, 2013, pp. 16159-16165.
Mu et al., "One-pot synthesis of tyrosine-stabilized fluorescent gold nanoclusters and its application as turn-on sensor for Al3+ ions and turn-off sensor for Fe3+ ions," The Royal Society of Chemistry, 2014, pp. 1-10.
Park et al., "A label-free method for detecting biological thiols based on blocking of Hg2+-quenching of fluorescent gold nanoclusters," Biosensors and Bioelectronics, vol. 45, 2013 (available online Feb. 4, 2013), pp. 65-69.
Selvaprakash et al., "Using protein-encapsulated gold nanoclusters as photoluminescent sensing probes for biomolecules," Biosensors and Bioelectronics, vol. 61, 2014 (available online May 10, 2014), pp. 88-94.
Su et al., "Immobilization of bovine serum albumin-protected gold nanoclusters by using polyelectrolytes of opposite charges for the development of the reusable fluorescent Cu2+-sensor," Biosensors and Bioelectronics, vol. 44, 2013 (available online Jan. 16, 2013), pp. 16-20.
Zhang et al., "Facile preparation of glutathione-stabilized gold nanoclusters for selective determination of chromium (III) and chromium (IV) in environmental water samples," Analytica Chimica Acta, vol. 770, 2013 (available online Jan. 28, 2013), pp. 140-146.
Zhang et al., "Glutathione-protected fluorescent gold nanoclusters for sensitive and selective detection of CU2+," Sensors and Actuators B, vol. 183, 2013 (available online Apr. 17, 2013), pp. 583-588.

\* cited by examiner

PROBE AND METHOD FOR DETECTING METAL IONS AND CHEMICAL/BIOCHEMICAL MOLECULES

BACKGROUND

Technical Field

The technical field relates to a probe for detecting metal ions and chemical/biochemical molecules, and in particular it relates to a method for manufacturing the same and a detection method utilizing the same.

Related Art

Metal ions participate in many important biochemical reactions in vivo. For example, the metal ions of Fe, Cu, Co, Mn, Zn, Ca, Mg, K, or Na are necessary to maintain life activity. These metal ions usually have functions such as transmitting nerve impulses, muscle contraction, cell-activity regulation, or interacting with biochemical molecules to change the configurations or effect of the biochemical molecules. In other words, the metal ions play important physiological roles in every bio-system. In addition, the heavy metal pollution from industry, i.e. lead, cadmium, and mercury, can be bioconcentrated into the human body through the food chain, thereby directly influencing human health and the natural environment. A method of analysis for quickly detecting metal ions is therefore called for. Conventional methods for detecting metal ions include atomic absorption spectroscopy, inductively coupled plasma mass spectrometry, atomic fluorescence spectroscopy, chemical titration, electrochemical analysis, and colorimetry. However, these methods usually have shortfalls such as requiring expensive instruments, demanding large sample volume, requiring complicated pre-treatment of a sample, and issues of non-immediate detection. As such, a simple, fast, and highly efficient method for detecting a trace amount of metal ions should be developed. If the method can be further applied to detect biochemical molecules, it will have a great practice meaning and market prospect.

SUMMARY

One embodiment of the disclosure provides a probe, comprising: a gold nanocluster; and a reducing agent partially capped on a surface of the gold nanocluster; wherein the probe is formed of reducing gold ions by the reducing agent, and the gold ions and the reducing agent have a molar ratio of 1:0.7 to 1:1.9.

One embodiment of the disclosure provides a method for detecting metal ions, comprising: providing a probe, wherein the probe includes: a gold nanocluster; and a reducing agent partially capped on a surface of the gold nanocluster, wherein the probe is formed of reducing gold ions by the reducing agent, and the gold ions and the reducing agent have a molar ratio of 1:0.7 to 1:1.9; and mixing the probe and an analyte solution to form a mixture, and analyzing the analyte solution to determine whether it contains specific metal ions or not by comparing the fluorescent spectra difference of the probe and the mixture.

One embodiment of the disclosure provides a method for detecting chemical/biochemical molecules, comprising: providing a probe, wherein the probe includes: a gold nanocluster; a reducing agent partially capped on a surface of the gold nanocluster; and metal ions chelated to the reducing agent, wherein the probe is formed of reducing gold ions by the reducing agent, and the gold ions and the reducing agent have a molar ratio of 1:0.7 to 1:1.9; and mixing the probe and an analyte solution to form a mixture, and analyzing the analyte solution to determine whether it contains specific chemical/biochemical molecules or not by comparing the fluorescent spectra difference of the probe and the mixture.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
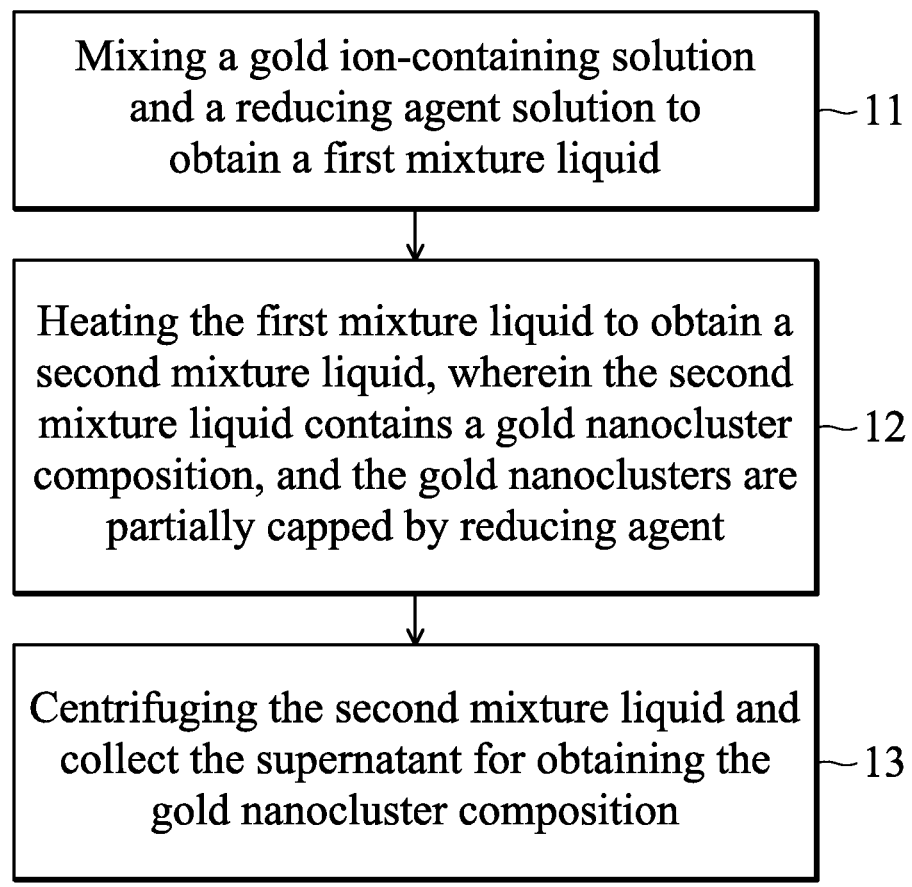
FIG. 1 shows a flow chart of preparing a gold nanocluster composition in one embodiment of the disclosure.

FIG. 1 shows a flow chart of preparing a fluorescent gold nanocluster composition in one embodiment of the disclosure. First, a gold ion-containing solution and a reducing agent solution are mixed to form a first mixture liquid in step 11. In one embodiment, the gold ion-containing solution can be a chloroauric acid solution, auric chloride solution, gold sulfide solution, or a combination thereof. The reducing agent can be glutathione (GSH). When the gold ions and the reducing agent have a molar ratio of 1:0.9 to 1:1.4, a gold nanocluster composition formed therefrom may simultaneously have dual fluorescence emission peaks, e.g. at a wavelength of 600-650 nm and 800-850 nm. When the gold ions and the reducing agent have a molar ratio of 1:0 to 1:0.6, a mixing liquid formed therefrom has no fluorescence. When the gold ions and the reducing agent have a molar ratio of 1:1.5 to 1:2, a gold nanocluster composition formed therefrom has deformed fluorescence emission peaks. The fluorescence emission at a wavelength of 700 nm of a gold nanocluster composition will be weakened by increasing the molar ratio of the reducing agent.

Subsequently, the first mixture liquid is heated to form a second mixture liquid in step 12. In one embodiment, the heating step can be performed by a general heating method such as with a dry bath heater or a microwave heater. In one embodiment, the heating step is performed by microwave power of 270 W to 450 W for a period of 10 minutes to 60 minutes. The gold ions cannot completely react to form a gold nanocluster composition by overly low microwave power or an overly short heating period. The gold ions easily form larger gold nanoparticles by overly high microwave power or an overly long heating period. The second mixture liquid formed by the heating process contains the fluorescent gold nanocluster compositions, wherein the gold nanoclusters are partially capped by reducing agent. The term "partially" means that not the entire surface of each of the gold nanoclusters is fully capped by reducing agent, and some unoccupied sites on the surface of the gold nanoclusters remain.

Finally, the second mixture liquid can be centrifuged in step 13 to collect the supernatant for obtaining the fluorescent gold nanocluster compositions. The solution containing fluorescent gold nanocluster compositions is stored at 4° C. for further use. In some embodiments, the rotation speed of the centrifugal step is 10000 rpm to 14000 rpm. In another embodiment, the factors of the centrifugal step such as rotation speed, rotation period, and rotation frequency are not limited. Only if the fluorescent gold nanocluster compositions can be separated by a set of centrifugal factors are the set of factors accepted.

In another embodiment, steps 11 to 13 are repeated, the difference being that the gold ions and the reducing agent have a molar ratio of 1:0.7 to 1:0.8, and the other process factors of the heating step and the centrifugal step are similar to the above embodiment. As such, the fluorescent gold nanoclusters are partially capped by the reducing agent, and the gold nanocluster compositions have a single fluorescence emission peak at a wavelength of 800 nm to 900 nm.

The fluorescent gold nanocluster compositions may serve as signal molecules due to their specific optical properties. The gold nanocluster compositions allow for easy modification for different applications, such as biomedicine (e.g. detection, imaging, and drug release therapy). The gold nanocluster compositions with the specific emission properties can be applied as a novel optoelectronic material or sensor for environmental safety, food safety, and elsewhere in the food industry.

In one embodiment, the fluorescent gold nanocluster compositions may serve as probes for detecting $Ag^+$, $Gd^{3+}$, $Zr^{4+}$, $Fe^{3+}$, $Ga^{3+}$, $Pb^{2+}$, $Eu^{3+}$, or $Cu^{2+}$. In another embodiment, the fluorescent gold nanocluster composition is prepared and then mixed with a chelating agent, such that the chelating agent is capped on the surface of the gold nanocluster. In one embodiment, the chelating agent can be glutathione, and the probe is utilized to detect $Ag^+$, $Gd^{3+}$, $Al^{3+}$, $Zr^{4+}$, $Fe^{3+}$, $Cd^{2+}$, $Ga^{3+}$, $Pb^{2+}$, $Eu^{3+}$, or $Cu^{2+}$. In another embodiment, the chelating agent can be N—N$\alpha$,N$\alpha$-bis (carboxymethyl)-L-lysine]-12-mercaptododecanamide, and the probe is utilized to detect $Co^{2+}$, $Ni^{2+}$, $Ag^+$, $Gd^{3+}$, $Al^{3+}$, $Zr^{4+}$, $Zn^{2+}$, $Fe^{3+}$, $Cd^{2+}$, $Ga^{3+}$, $Pb^{2+}$, $Eu^{3+}$, or $Cu^{2+}$. The method of detecting metal ions by the probe can be mixing the probe and an analyte solution to form a mixture, and comparing the difference of the fluorescent spectra between the probe and the mixture, thereby analyzing the analyte solution to determine whether it contains specific metal ions or not.

In one embodiment, the fluorescent gold nanocluster composition (with a surface capped by the chelating agent) is mixed with metal ions, such that the metal ions are chelated to the reducing agent and the chelating agent to form a probe for detecting chemical/biochemical molecules. In one embodiment, the reducing agent includes glutathione, the chelating agent includes glutathione, the metal ions include $Gd^{3+}$, and the chemical/biochemical molecules contain phosphate groups. For example, the chemical/biochemical molecules can be sodium phosphate, sodium pyrophosphate, or deoxyadenosine triphosphate. In one embodiment, the fluorescent gold nanocluster composition (with a surface not capped any chelating agent) can be mixed with metal ions, such that the metal ions are chelated to the reducing agent to form a probe for detecting chemical/biochemical molecules. In one embodiment, the reducing agent includes glutathione, the metal ions include $Gd^{3+}$, and the chemical/biochemical molecules contain phosphate groups. For example, the chemical/biochemical molecules can be sodium phosphate, sodium pyrophosphate, or deoxyadenosine triphosphate.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Preparation of Fluorescent Gold Nanocluster Compositions

Example 1

5 mM chloroauric acid ($HAuCl_4$) solution and 5 mM glutathione (L-glutathione, GSH) solution were prepared. 0.2 mL of $HAuCl_4$ solution and 0.2 mL of GSH solution were added to a microcentrifuge tube, wherein the molar ratio of $HAuCl_4$ and GSH was 1:1. The tube was then completely shaken for 5 minutes using a vortex mixer to obtain a first mixture liquid. The microcentrifuge tube was opened and then put into a domestic microwave oven, heated by microwave power of 270 W for 30 minutes, and then heated by microwave power of 450 W for 30 minutes to obtain a second mixture liquid. The microcentrifuge tube was cooled to room temperature and then centrifuged at 12000 rpm for 10 minutes. The supernatant was collected to obtain a liquid containing the fluorescent gold nanocluster compositions. Concentrations of $HAuCl_4$ solution and GSH solution could be controlled to fine-tune the fluorescence emission peak range of the gold nanocluster compositions.

Example 2

5 mM $HAuCl_4$ solution and 5 mM GSH solution were prepared. 0.2 mL of $HAuCl_4$ solution and 0.2 mL of GSH solution were added to a glass sample vial, wherein the molar ratio of $HAuCl_4$ and GSH was 1:1. The vial was then completely shaken for 10 seconds using a vortex mixer to obtain a first mixture liquid. The glass sample vial was opened and then put into a dry bath heater, heated from room temperature to 120° C. for 10 minutes, and then heated at 120° C. for 50 minutes to obtain a second mixture liquid. The glass sample vial was cooled to room temperature and then the solution was centrifuged at 12000 rpm for 10 minutes. The supernatant was collected to obtain a liquid containing the fluorescent gold nanocluster compositions.

Example 3

Figure 3A:
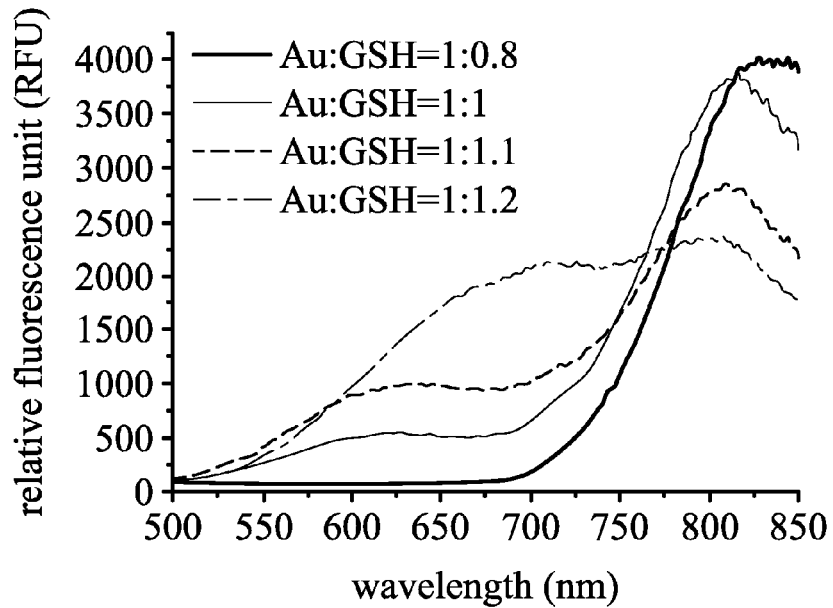
FIGS. 3A-3B, 4, 5, and 6 show the specific fluorescence spectra of the gold nanocluster compositions prepared at different molar ratios of gold ions to glutathione in embodiments of the disclosure.
Figure 3B:
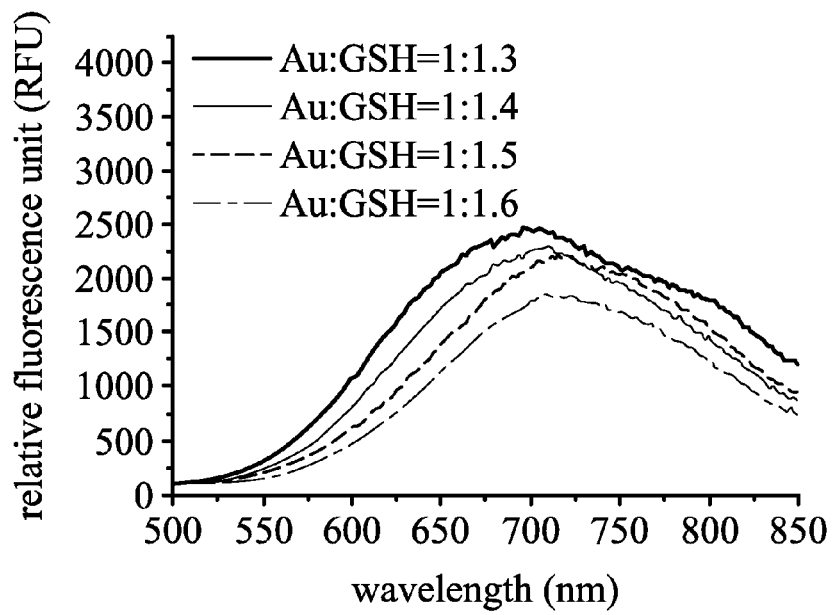

Example 3 was similar to Example 1, and the difference in Example 3 was the concentration of GSH solution being changed to achieve different molar ratios of $HAuCl_4$ and GSH, such as Au:GSH=1:1.1, 1:1.2, 1:1.3, 1:1.4, 1:1.5, and 1:1.6. When the Au:GSH was 1:1.1, the gold nanocluster compositions still had dual fluorescence emission peaks. When the Au:GSH was 1:1.2, the fluorescence emission peaks of the gold nanocluster compositions began to deform as shown in FIGS. 3A-3B.

Example 4

Figure 4:
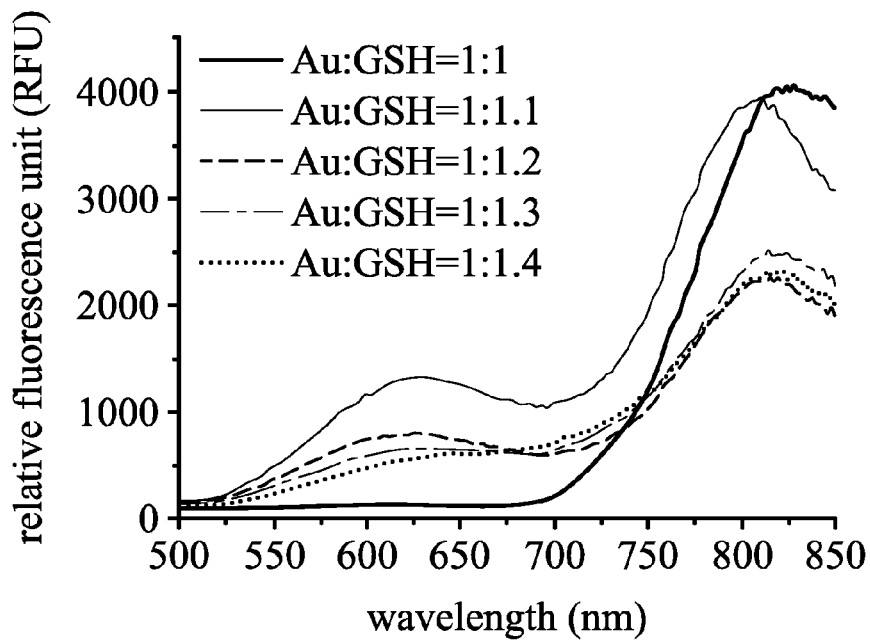

Example 4 was similar to Example 2, and the difference in Example 4 was the concentration of GSH solution being changed to achieve different molar ratios of $HAuCl_4$ and GSH, such as Au:GSH=1:1.1, 1:1.2, 1:1.3, and 1:1.4. The gold nanocluster compositions had dual fluorescence emission peaks, as shown in FIG. 4.

Example 5

Example 5 was similar to Example 1, and the difference in Example 5 was the concentration of GSH solution being changed to achieve a different molar ratio of $HAuCl_4$ and GSH, such as Au:GSH=1:0.8. The fluorescence emission spectrum of the gold nanocluster compositions is shown in FIG. 3A. Note that the gold nanocluster compositions prepared by above Au:GSH molar ratio only has a single fluorescence peak at the near-infrared region with a wavelength greater than 800 nm, other than dual fluorescence emission peaks at a wavelength of 600-650 nm and 800-850 nm.

Comparative Example 1

Figure 5:
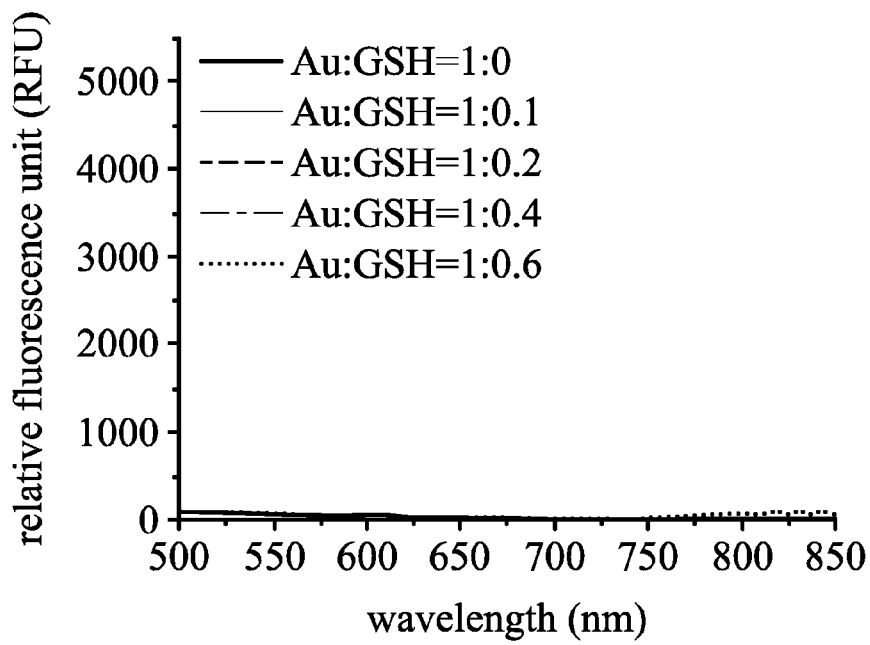

Comparative Example 1 was similar to Example 1, and the difference in Comparative Example 1 was the concentration of GSH solution being changed to achieve different molar ratios of $HAuCl_4$ and GSH, such as Au:GSH=1:0, 1:0.1, 1:0.2, 1:0.4, and 1:0.6. The products prepared from the above Au:GSH molar ratios had no fluorescent properties, as shown in FIG. 5.

Comparative Example 2

Figure 6:
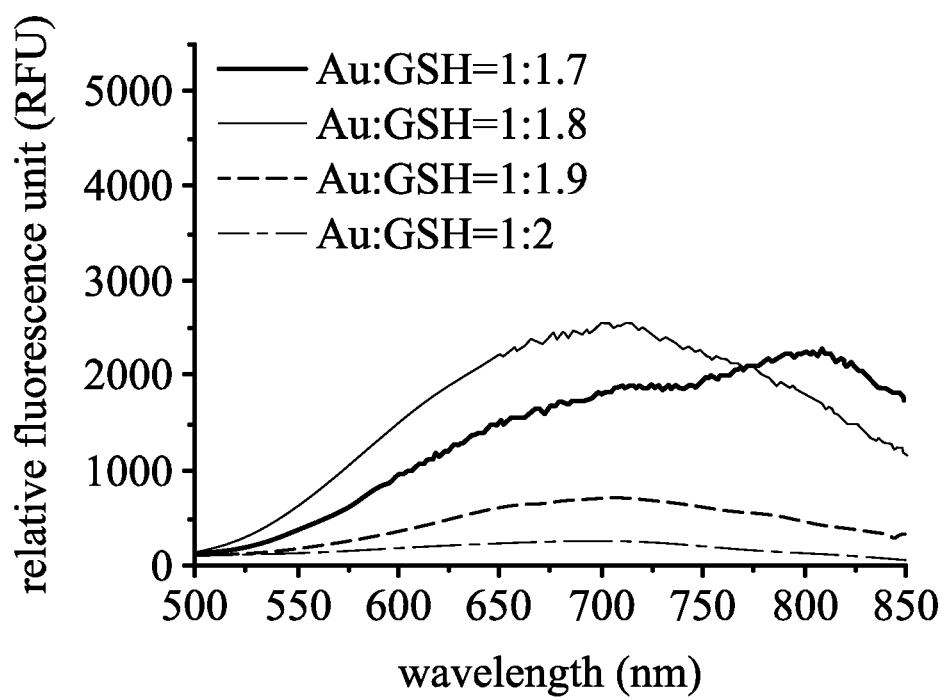
Figure 7A:
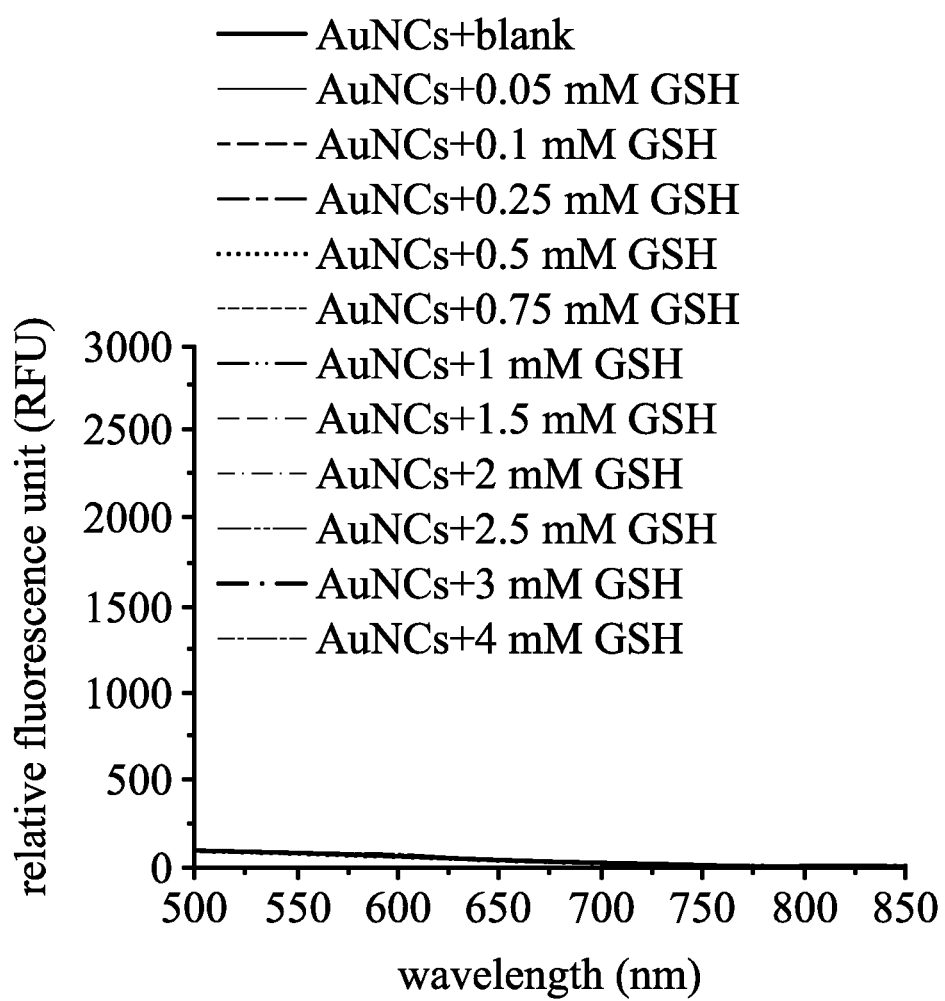
FIGS. 7A-7E and 8A-8E show the fluorescence spectra of the gold nanocluster compositions (prepared at different molar ratios of gold ions to glutathione) detecting thiol-containing compounds from liquid analytes in embodiments of the disclosure.
Figure 7B:
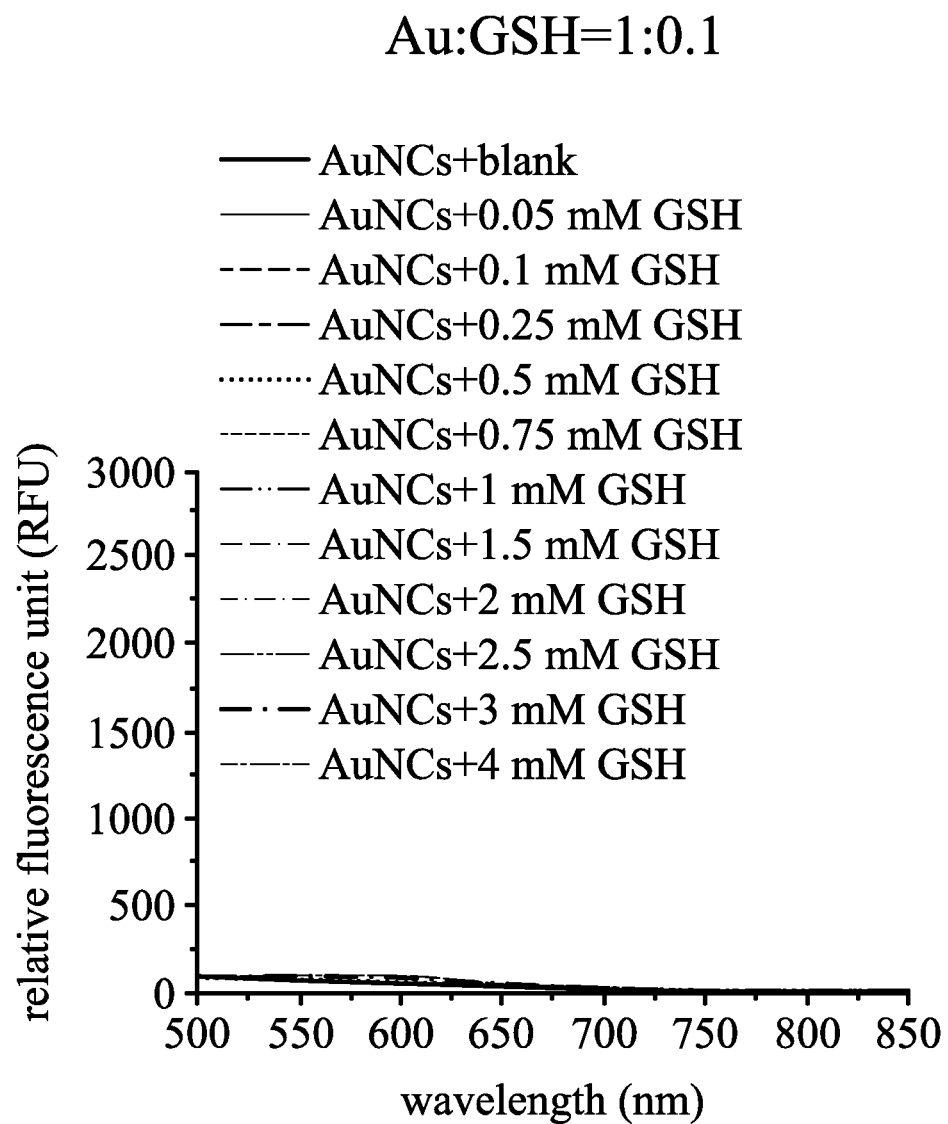
Figure 7C:
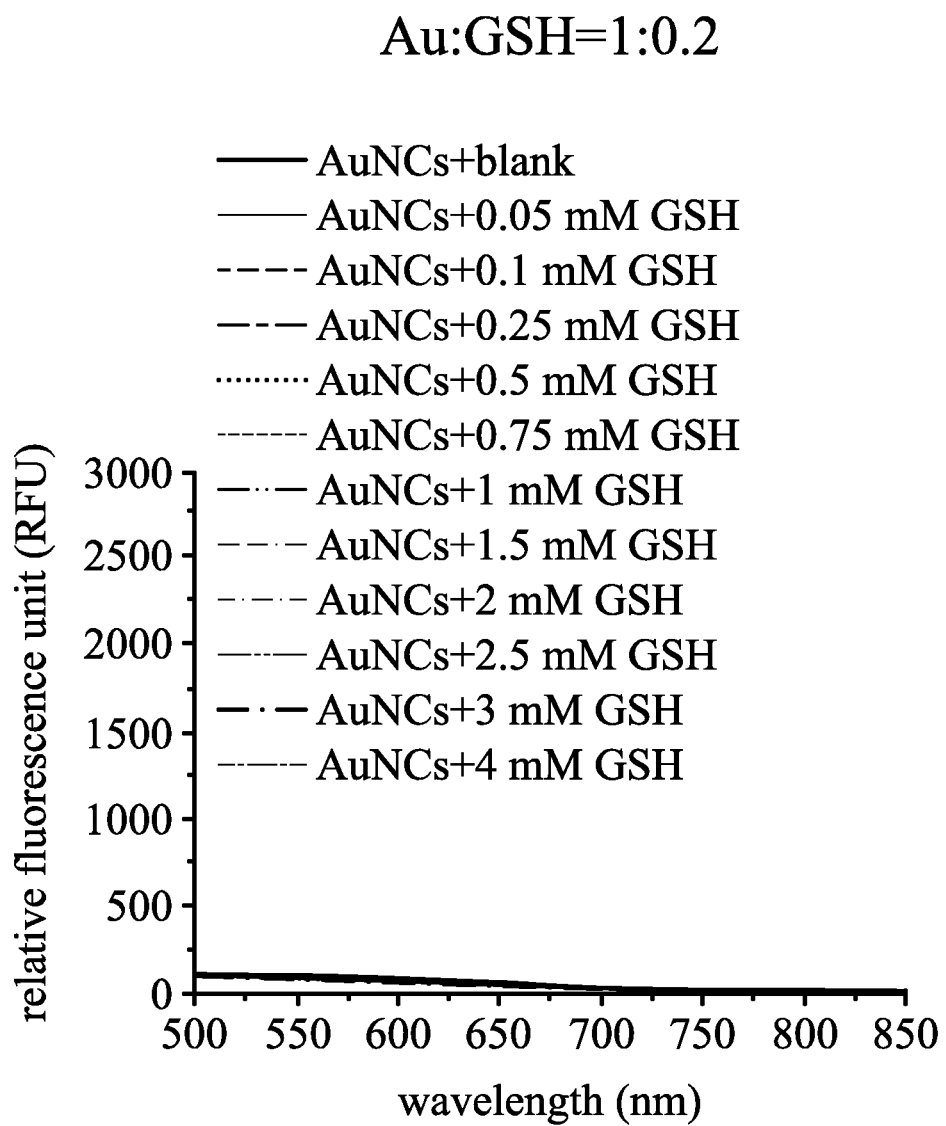
Figure 7D:
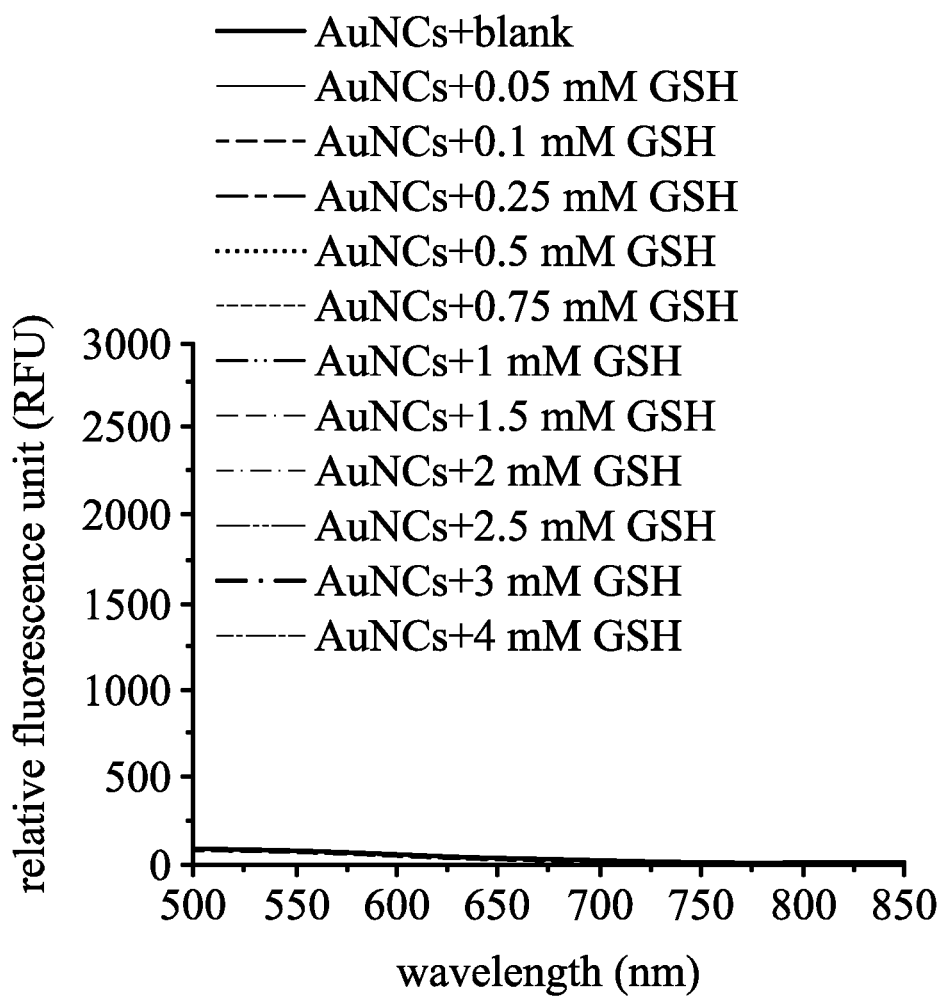
Figure 7E:
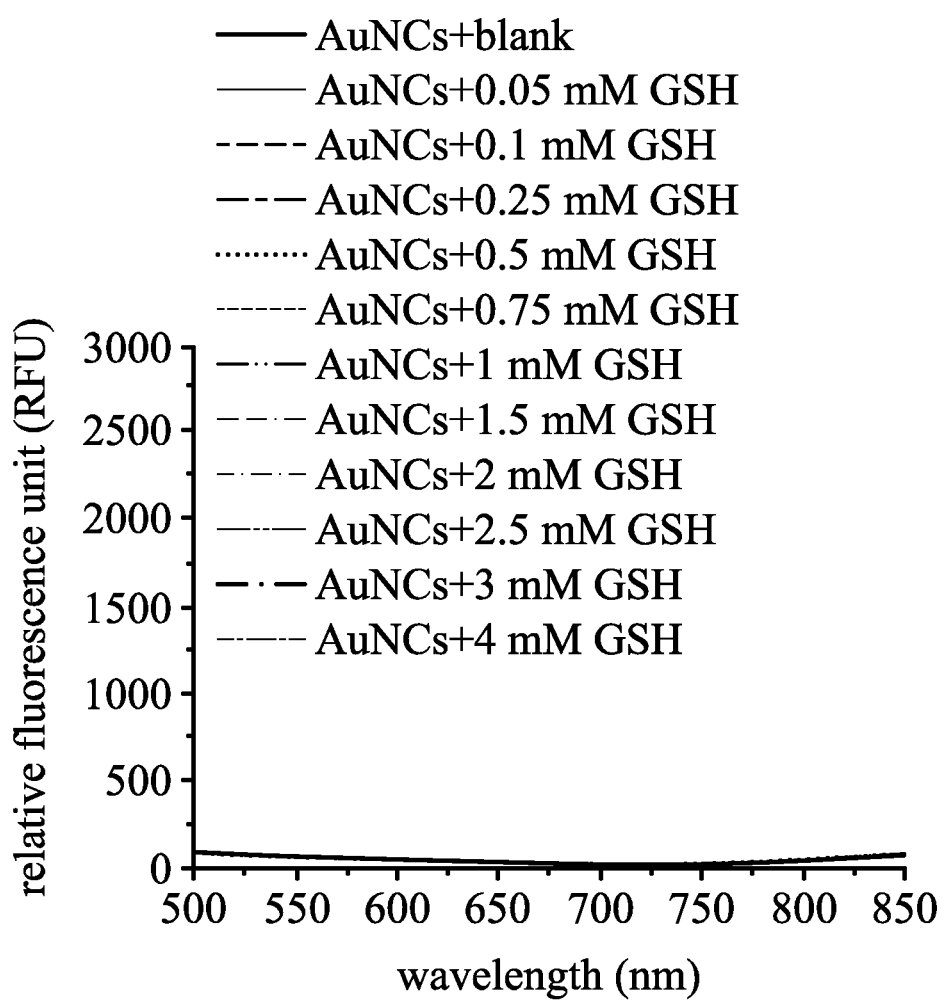
Figure 8A:
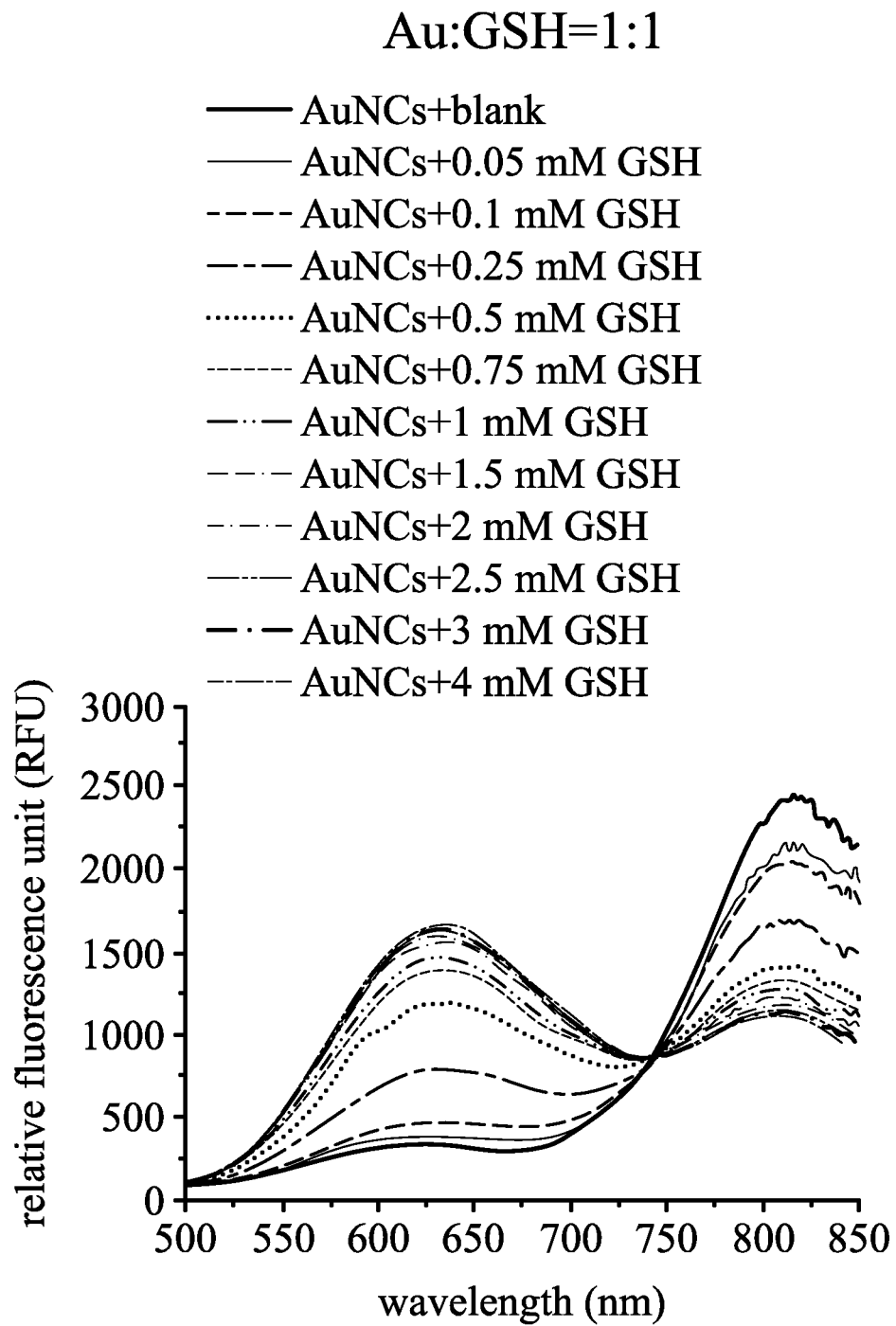
Figure 8B:
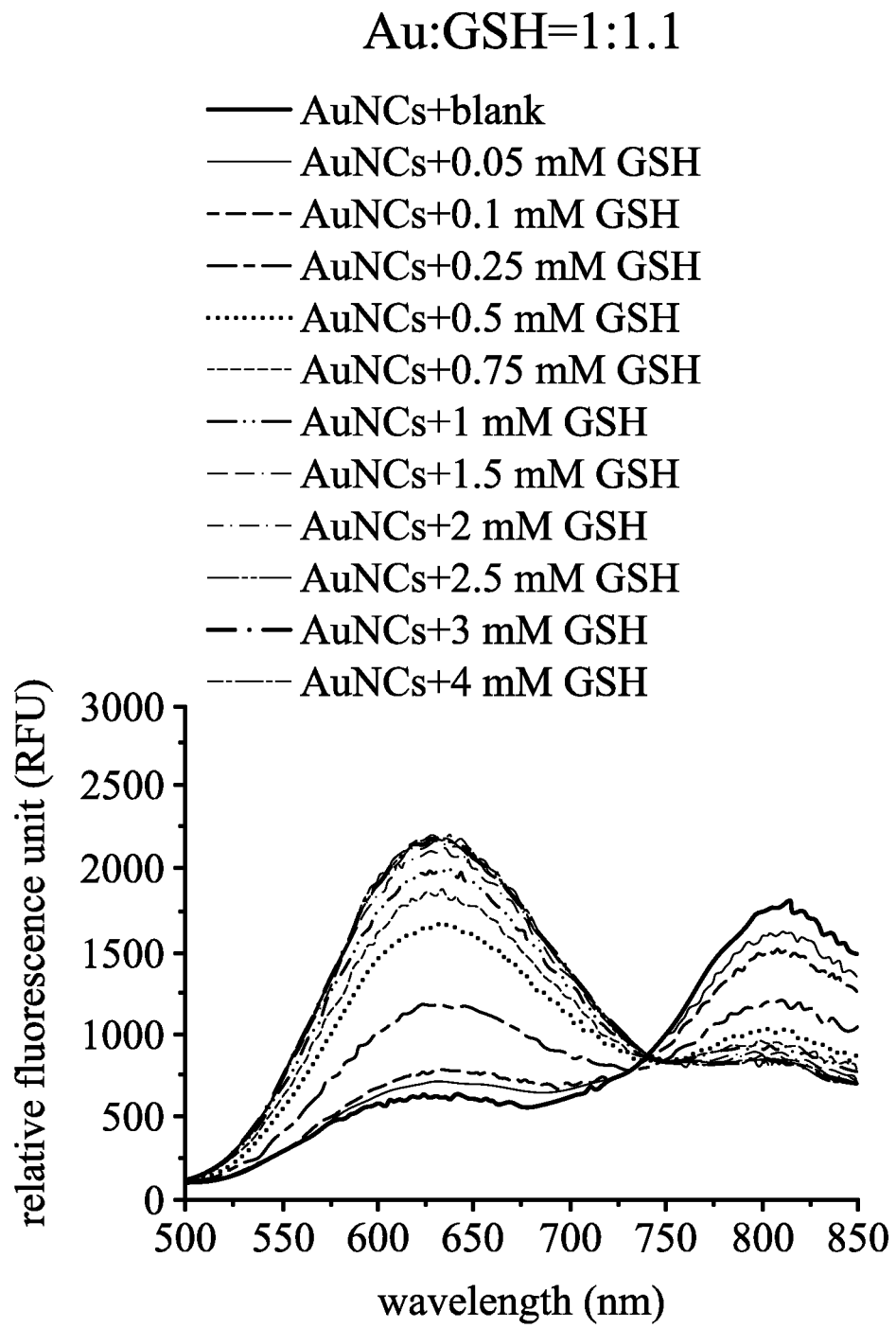
Figure 8C:
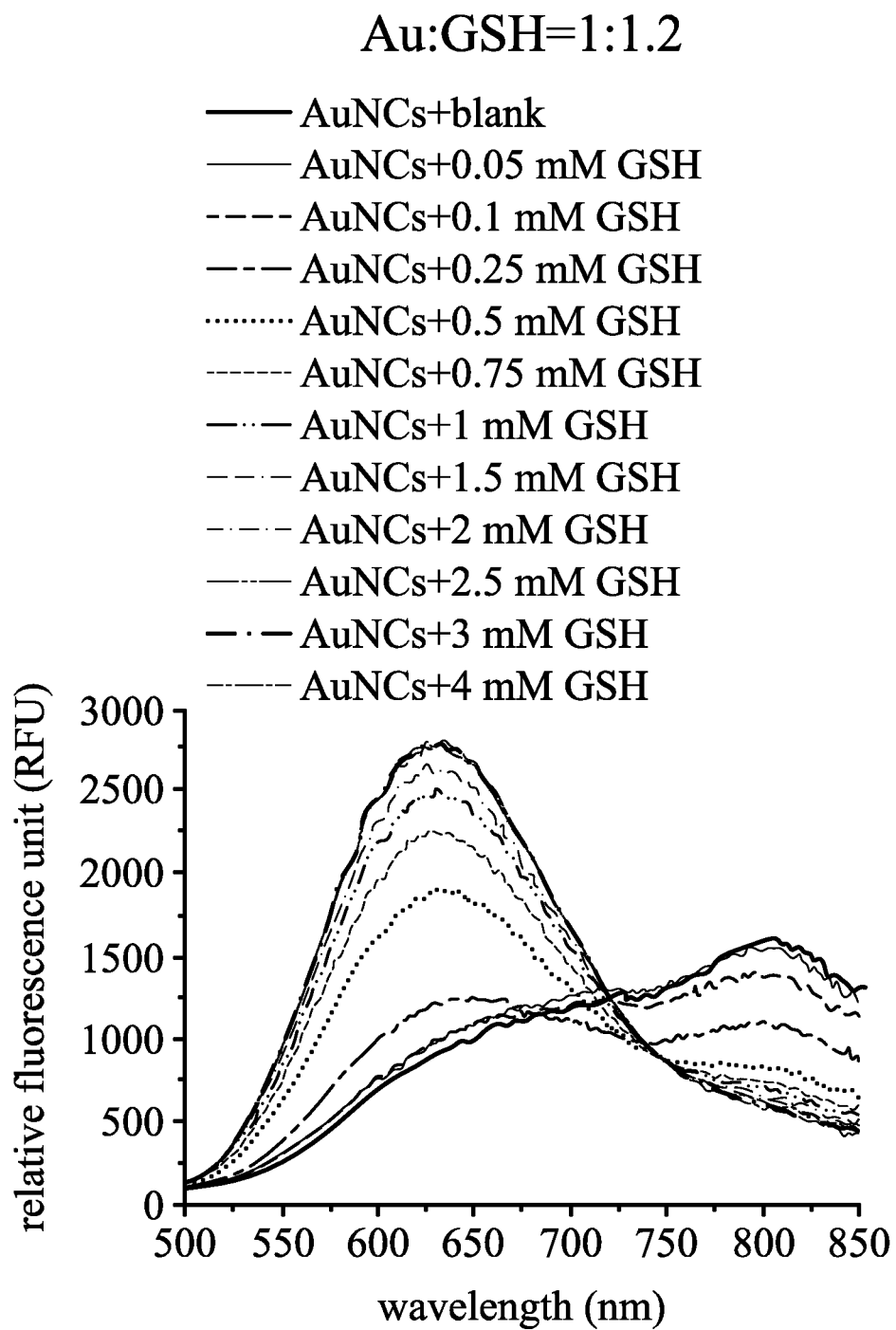
Figure 8D:
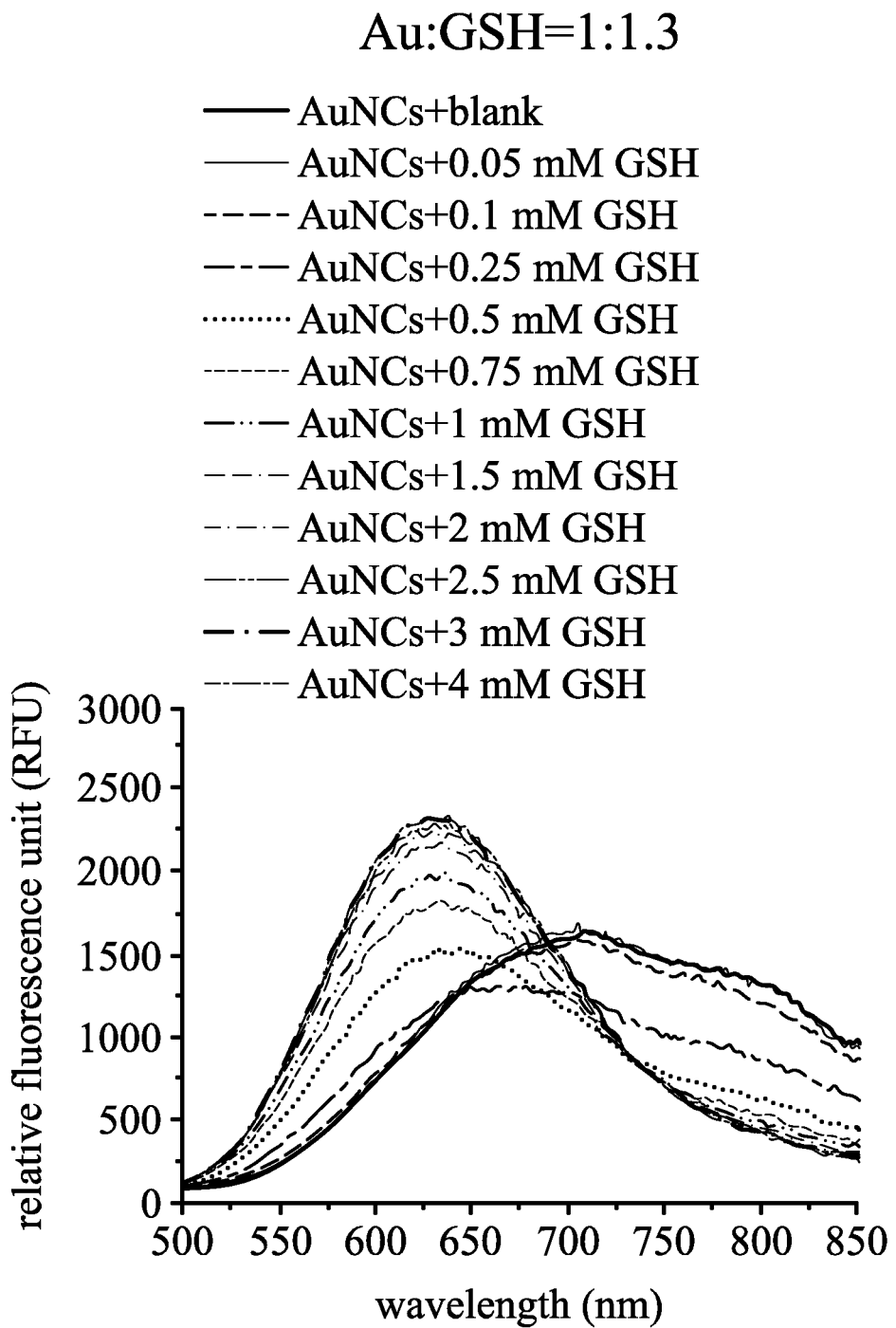
Figure 8E:
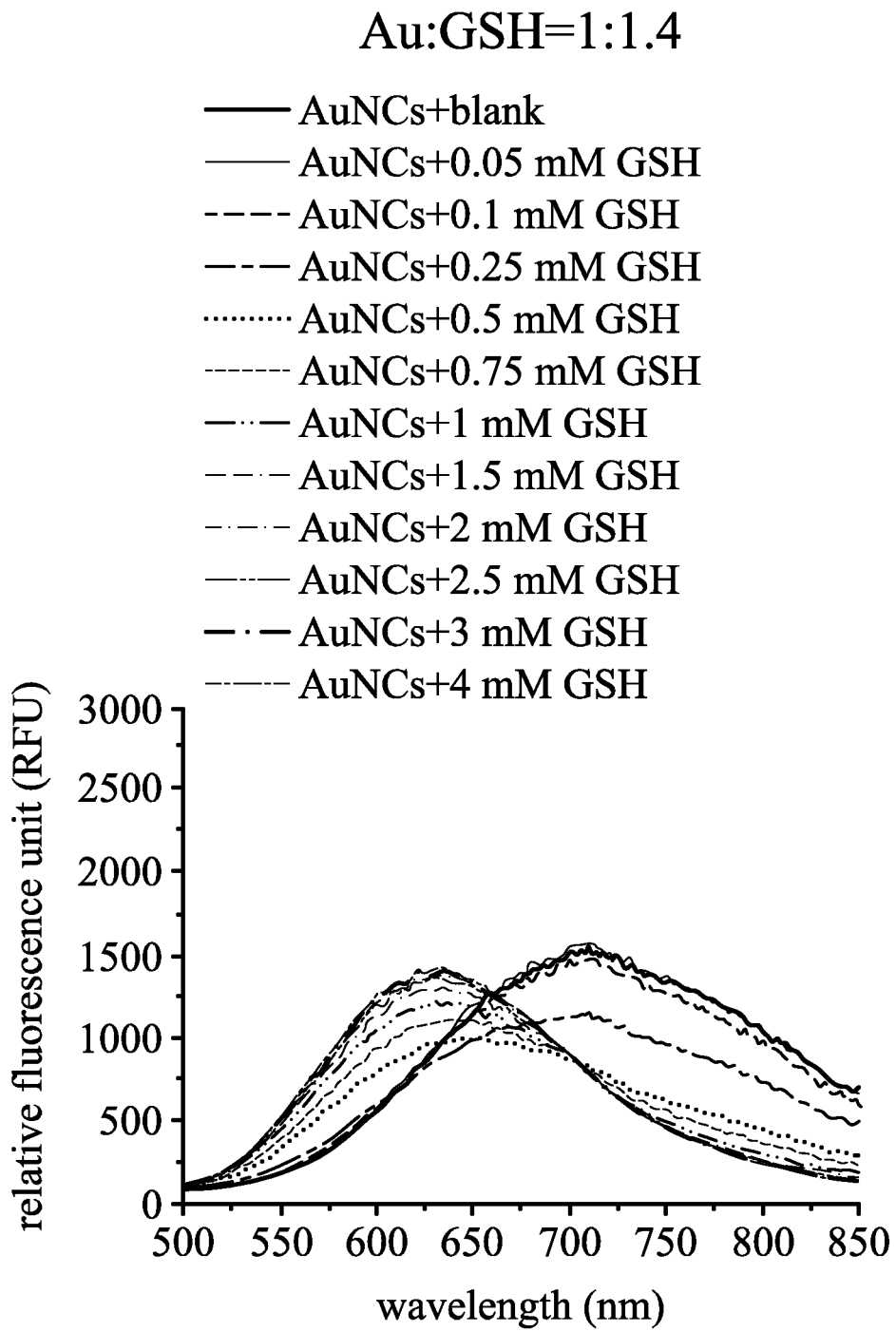
Figure 9A:
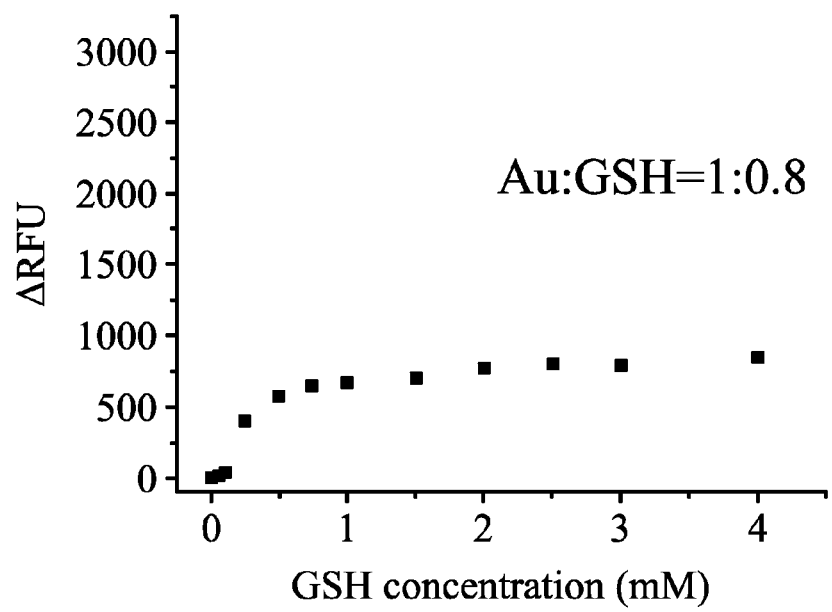
FIGS. 9A-9D, 10A-10D, and 11A-11D show the change of fluorescence intensity of the gold nanocluster compositions (prepared at different molar ratios of gold ions to glutathione) detecting thiol-containing compounds from liquid analytes in embodiments of the disclosure.
Figure 9B:
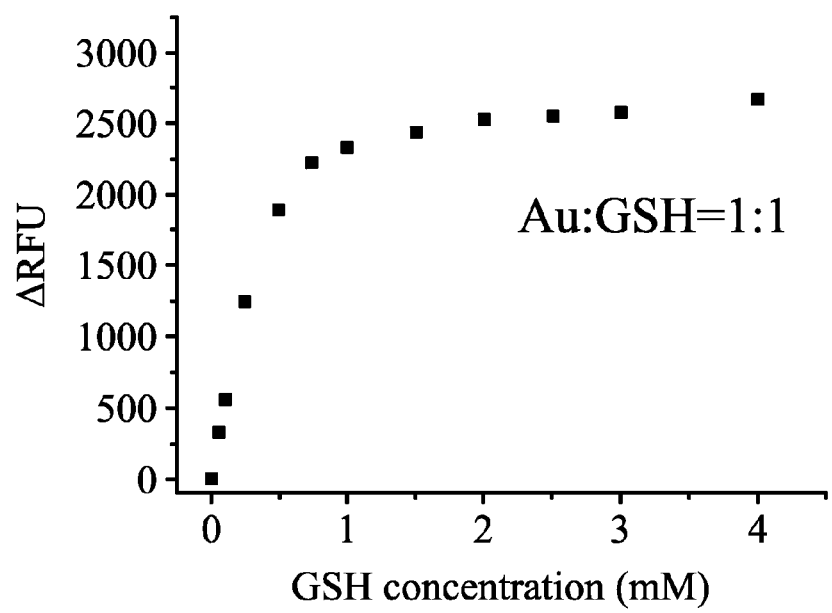
Figure 9C:
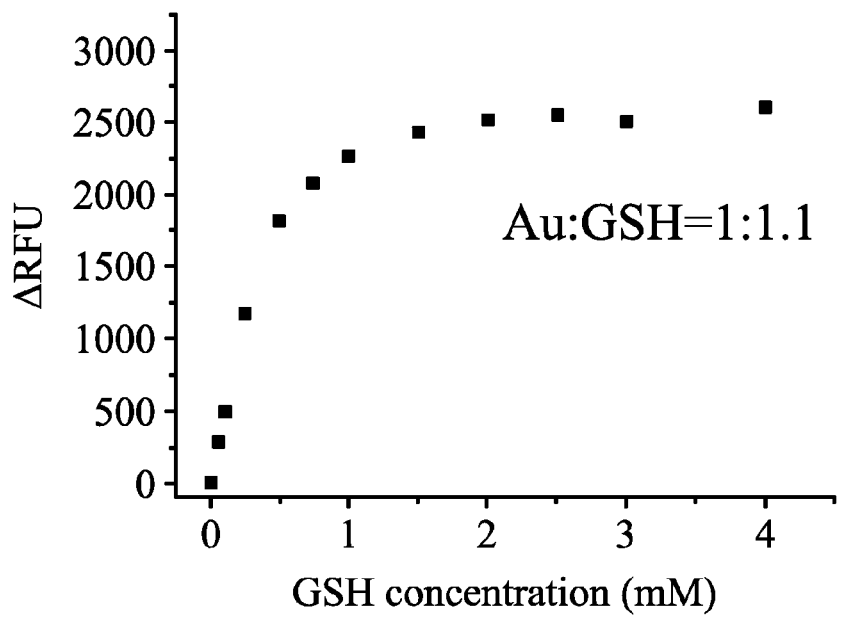
Figure 9D:
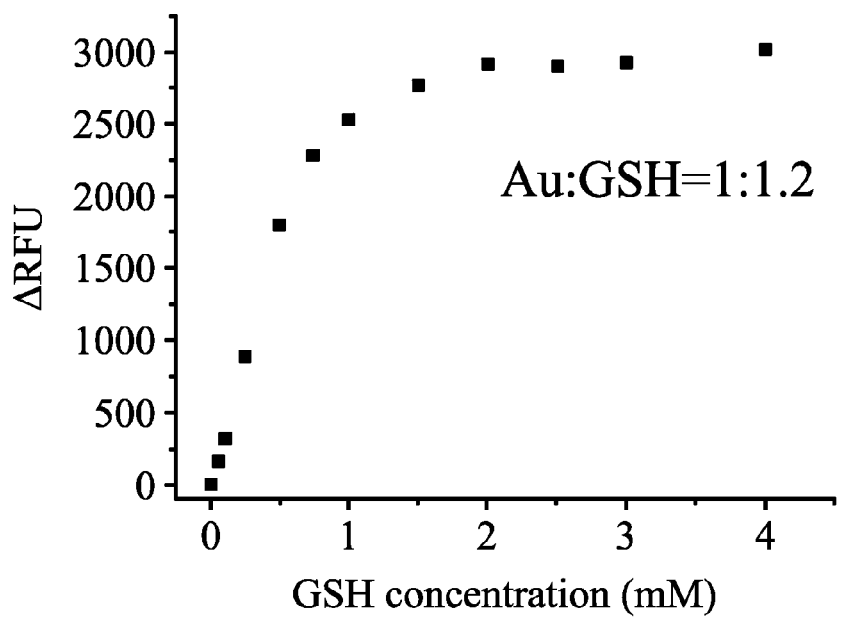
Figure 10A:
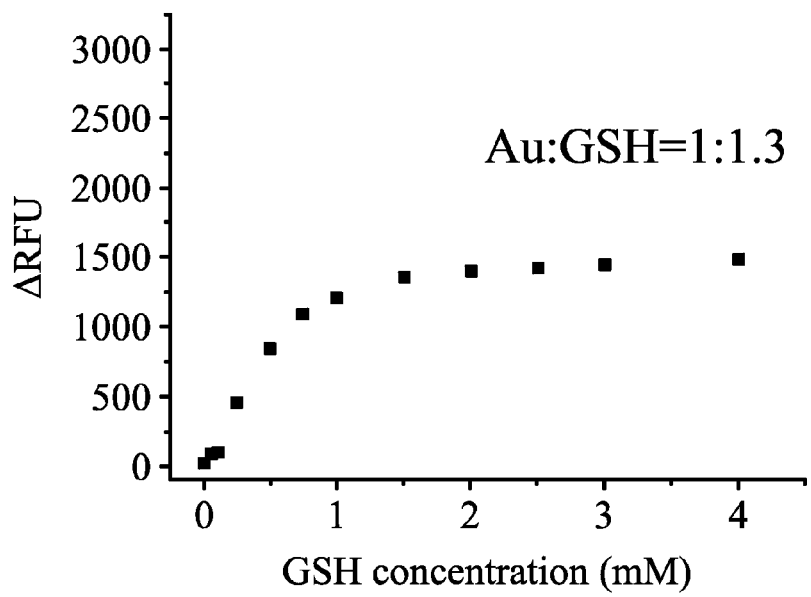
Figure 10B:
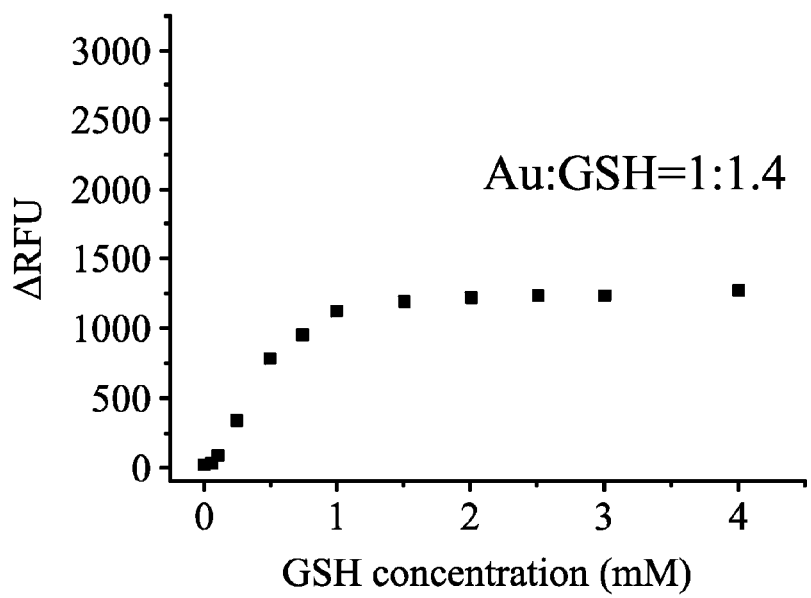
Figure 10C:
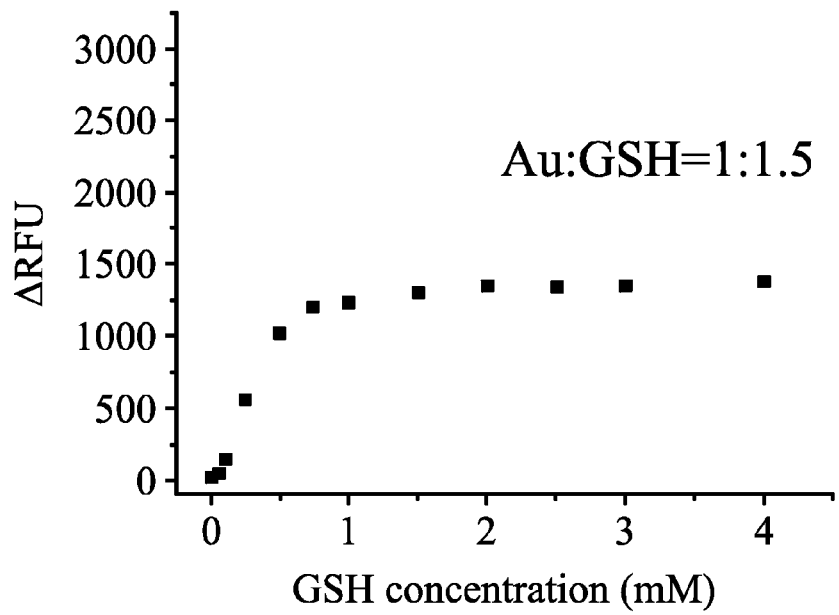
Figure 10D:
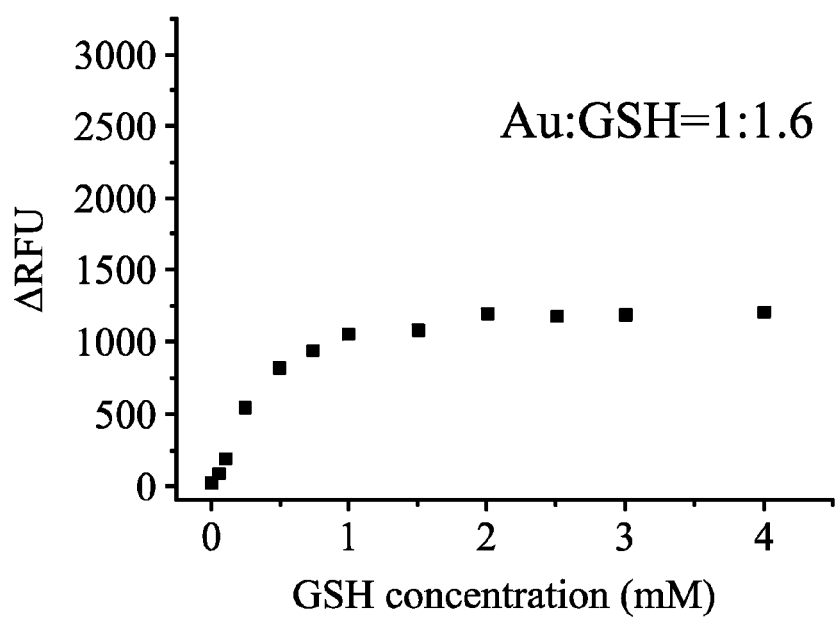

Comparative Example 2 was similar to Example 1, and the difference in Comparative Example 2 was the concentration of GSH solution being changed to achieve different molar ratios of $HAuCl_4$ and GSH, such as Au:GSH=1:1.7, 1:1.8, 1:1.9, and 1:2. The products prepared from the above Au:GSH molar ratios had only one fluorescence emission peak around wavelength of 700 nm. The emission intensities of the products were gradually decreased by increasing the GSH molar ratios, as shown in FIG. 6.

Proof of the Gold Nanoclusters being Partially Capped by GSH

15 μL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM) were added to 15 μL of the products in Comparative Example 1 (Au:GSH=1:0, 1:0.1, 1:0.2, 1:0.4, and 1:0.6) in the microwell plate, and then evenly mixed for 1 minute. The microwell plate was put into a fluorescence spectroscopy analysis system, and then excited by a light beam with wavelength of 365 nm to analyze the fluorescent properties of the mixtures. As shown in FIGS. 7A-7E, the products in Comparative Example 1 had no obvious fluorescence emission change after adding GSH solutions.

15 μL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM) were added to 15 μL of the liquid products in Example 1 (Au:GSH=1:1) and Example 3 (Au:GSH=1:1.1, 1:1.2, 1:1.3, and 1:1.4) in the microwell plate, and then evenly mixed for 1 minute. The microwell plate was put into a fluorescence spectroscopy analysis system, and then excited by a light beam with wavelength of 365 nm to analyze the fluorescent properties of the mixtures. As shown in FIGS. 8A-8E, the gold nanocluster compositions in Examples 1 and 3 had enhanced fluorescence intensities at a wavelength of 600-650 nm and weakened fluorescence intensities at a wavelength of 800-850 nm after adding GSH solutions. Especially when the Au:GSH molar ratios were 1:1, 1:1.1, and 1:1.2 for preparing the gold nanocluster compositions, the intensities of fluorescence emission peak significantly changed. Since it is hypothesized that the fluorescence of gold nanoclusters originates from the charge transfer between the ligands and gold nanocluster core through the Au—S bonds, as inferred from the above result, the gold nanoclusters were partially capped by GSH. Therefore, the gold nanocluster compositions still had unoccupied sites for further bonding to additional GSH, thereby changing the fluorescence emission intensities thereof.

When the Au:GSH molar ratios were 1:1.3 to 1:1.4, the products had deformed and shifted fluorescence emission spectra with minor intensity changes after adding 15 µL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM). As inferred from the above result, using higher GSH molar ratio for preparing the gold nanocluster compositions resulted in more GSH bonded on the surface of the gold nanoclusters. Therefore, fewer unoccupied sites on the surface of the gold nanoclusters could be bonded to the added GSH.

Analysis of the Fluorescence Emission Peak Intensity of the Gold Nanocluster Compositions after Adding Further GSH The sum of the increase of the fluorescence emission intensity at a wavelength of 630 nm and the decrease of the fluorescence emission intensity at a wavelength of 810 nm was defined as ΔRFU for revealing the relation between the change of fluorescence emission intensity and the concentration of GSH. While the Au:GSH molar ratios were 1:0.8 to 1:1.2, the ΔRFUs as a function of the concentration of the additional added GSH are shown in FIGS. 9A-9D. Because GSH simultaneously served as the reducing agent and the capping agent, as inferred from the above result, lower GSH concentration used during the synthesis tend to form larger gold nanocluster compositions with lower amounts of Au (I) on the surface for bonding to thiols. Thereby causing fewer change of the fluorescence emission intensity after adding additional GSH. The higher GSH concentration used during the synthesis should form smaller gold nanocluster compositions with higher amounts of Au (I) on the surface for bonding to thiols. As such, the fluorescence emission intensity changed significantly after adding additional thiols. While the Au:GSH molar ratios were 1:0.8 to 1:1.2, the ΔRFUs as a function of the concentration of the additional added GSH are shown in FIGS. 9A-9D.

In another example, the Au:GSH molar ratios were 1:1.3 to 1:1.6, such that the surface of the gold nanoclusters was capped by more GSH. As such, their fluorescence emission peak intensity changes were less and saturated earlier after adding additional GSH, as shown in FIGS. 10A-10D.

Figure 11A:
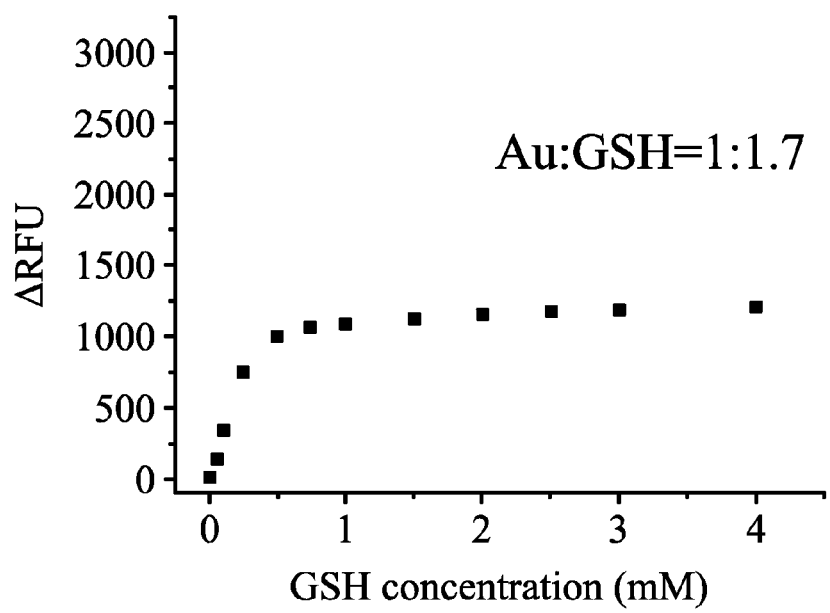
Figure 11B:
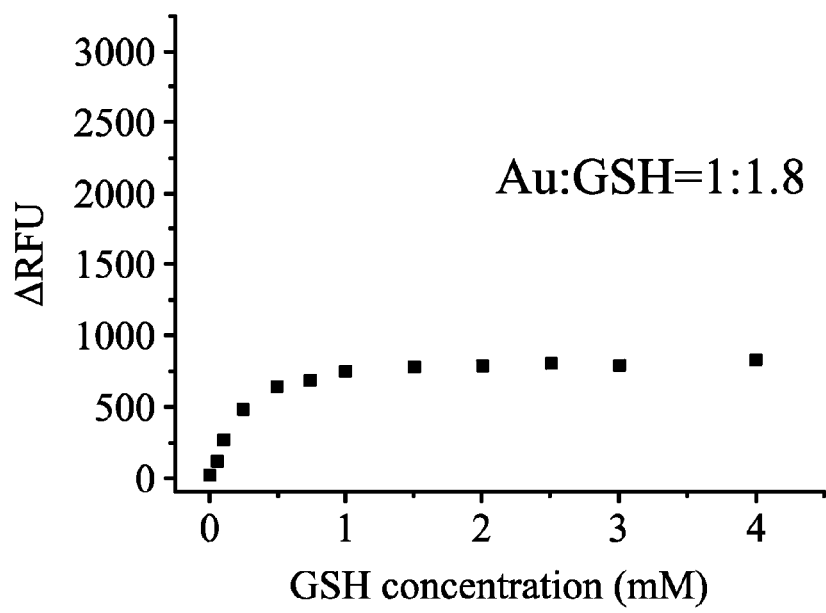
Figure 11C:
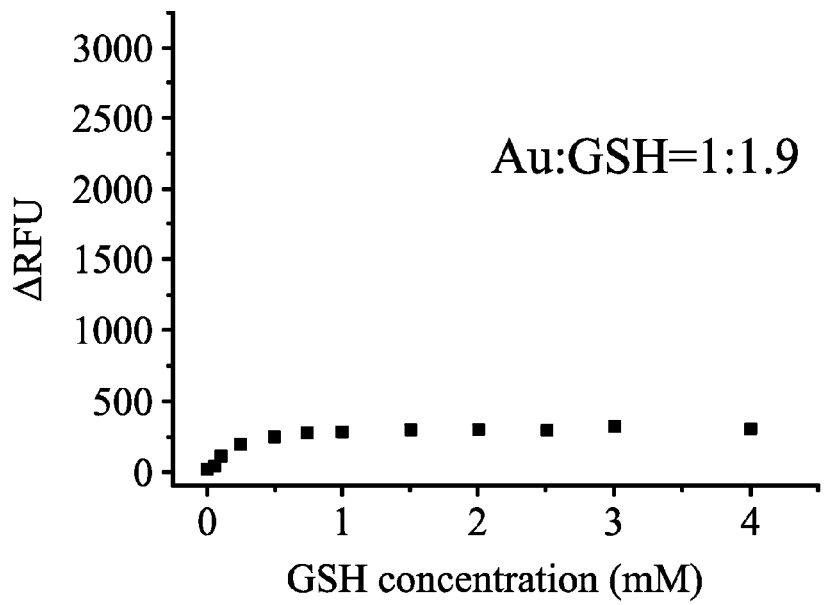
Figure 11D:
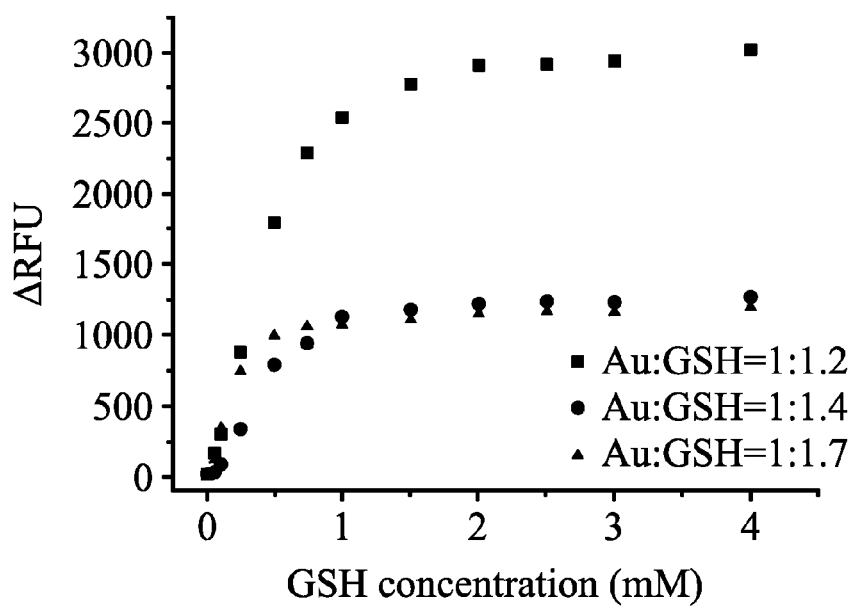

In a further example, the Au:GSH molar ratios were 1:1.7 to 1:1.9, such that the surface of the gold nanoclusters was capped by more GSH. As such, their fluorescence emission peak intensity changes were less and saturated earlier after adding additional GSH, as shown in FIGS. 11A-11C. FIG. 11D shows a comparison of the Au:GSH molar ratios of 1:1.2, 1:1.4, and 1:1.7.

Referring to the synthesis of the disclosure with Au:GSH molar ratios of 1:0.8 to 1:1.2, the gold nanocluster compositions prepared by more GSH could have enhanced fluorescence emission peaks at a wavelength of 600-650 nm and weakened fluorescence emission peaks at a wavelength of 800-850 nm. When the gold nanocluster compositions were prepared with Au:GSH molar ratios of 1:1.8 to 1:1.9, their fluorescence emission peak intensity changes were less and saturated earlier. Simultaneously, the fluorescent gold nanocluster compositions prepared with a higher GSH concentration tended to be saturated earlier. As a result, the Au:GSH molar ratio can be controlled to fine-tune the amount of GSH capped on the surface of the gold nanoclusters.

Figure 12:
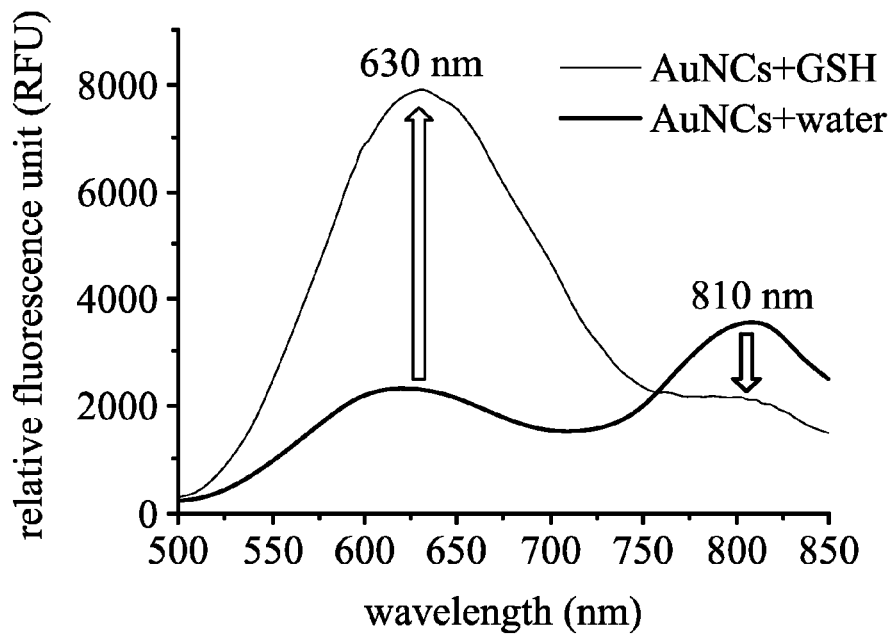
FIG. 12 shows the fluorescence spectrum obtained from the mixture solution of the gold nanocluster compositions and water (or glutathione aqueous solution) in one embodiment of the disclosure.

Furthermore, the fluorescence emission spectra of the gold nanocluster compositions changed after reacting with additional added GSH, as shown in FIG. 12. For example, the fluorescence intensity at a wavelength of 630 nm was enhanced, and the fluorescence intensity at a wavelength of 810 nm was weakened. Accordingly, the gold nanocluster compositions might serve as sensors for thiol analytes.

Although the above fluorescence emission peak changes could be determined by fluorescence spectra, the fluorescence emission intensity changes could also be seen with the naked eye.

Preparation of Probes for Detecting Metal Ions

Probe A

The fluorescent gold nanocluster composition in Example 3 (Au:GSH=1:1.1) was diluted 10 times by de-ionized water. 15 µL of the diluted solution was mixed with 15 µL of water to obtain Probe A.

Probe B

The fluorescent gold nanocluster composition in Example 3 (Au:GSH=1:1.1) was diluted 10 times by de-ionized water. 15 µL of the diluted solution was mixed with 15 µL of a GSH aqueous solution (0.1 mM) to obtain Probe B, in which the further GSH serves as a chelating agent.

Probe C

The fluorescent gold nanocluster composition in Example 3 (Au:GSH=1:1.1) was diluted 10 times by a mixing solution of de-ionized water and dimethyl sulfoxide (v/v=7/2). 15 µL of the diluted solution was mixed with 15 µL of a dimethyl sulfoxide solution of N—Nα,Nα-bis(carboxymethyl)-L-lysine]-12-mercaptododecanamide (thiolated NTA, 0.05 mM) to obtain Probe C, in which the further thiolated NTA serves as a chelating agent.

Probe D

The fluorescent gold nanocluster composition in Example 3 (Au:GSH=1:1.1) was diluted 10 times by de-ionized water. 15 µL of the diluted solution was mixed with 15 L of a GSH aqueous solution (0.2 mM) to obtain Probe D, in which the further GSH serves as a chelating agent.

Probe E

The fluorescent gold nanocluster composition in Example 3 (Au:GSH=1:1.1) was diluted 10 times by de-ionized water. 15 µL of the diluted solution was mixed with 15 µL of a GSH aqueous solution (0.2 mM) and 15 µL of $Gd^{3+}$ ionic solution (100 µM) for 10 minutes to obtain Probe E, in which the further GSH serves as a chelating agent and the further $Gd^{3+}$ ions serve as metal ions.

Detection of Metal Ions

Example 6

Figure 13A:
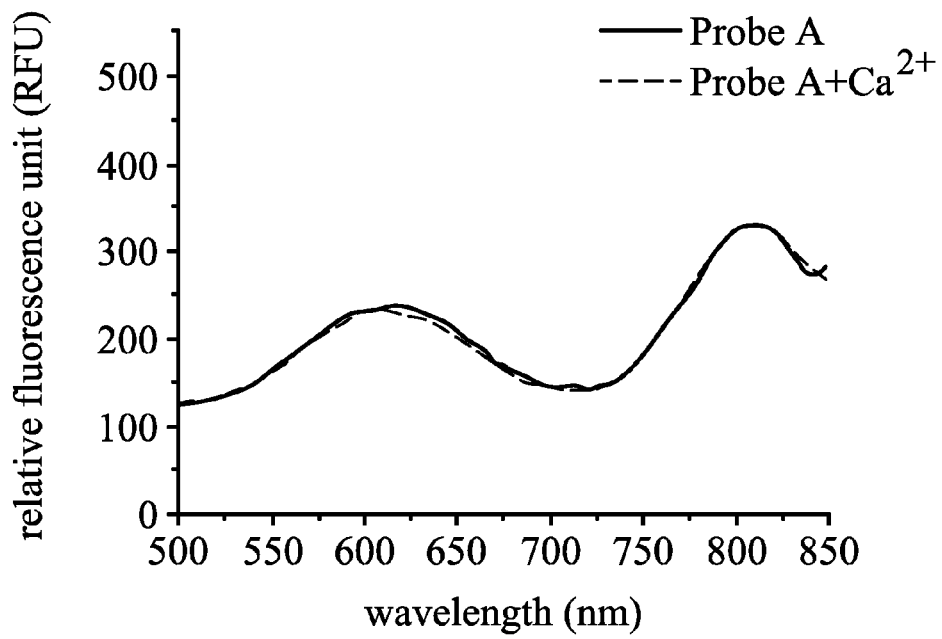
FIGS. 13A, 13B, and 13C show comparisons of fluorescence spectra of Probes A, B, and C before and after being mixed with a $Ca^{2+}$ ionic solution in one embodiment of the disclosure.
Figure 13B:
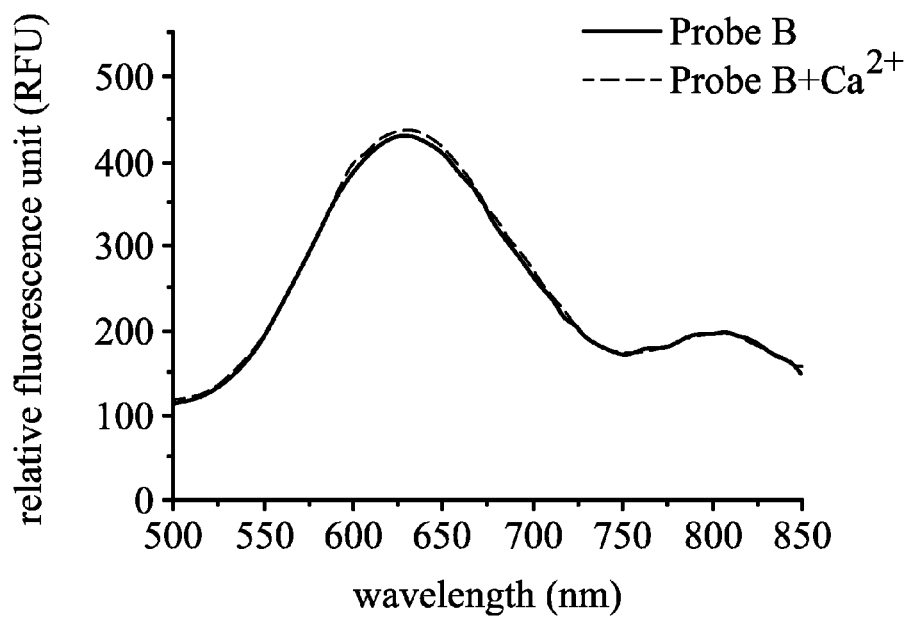
Figure 13C:
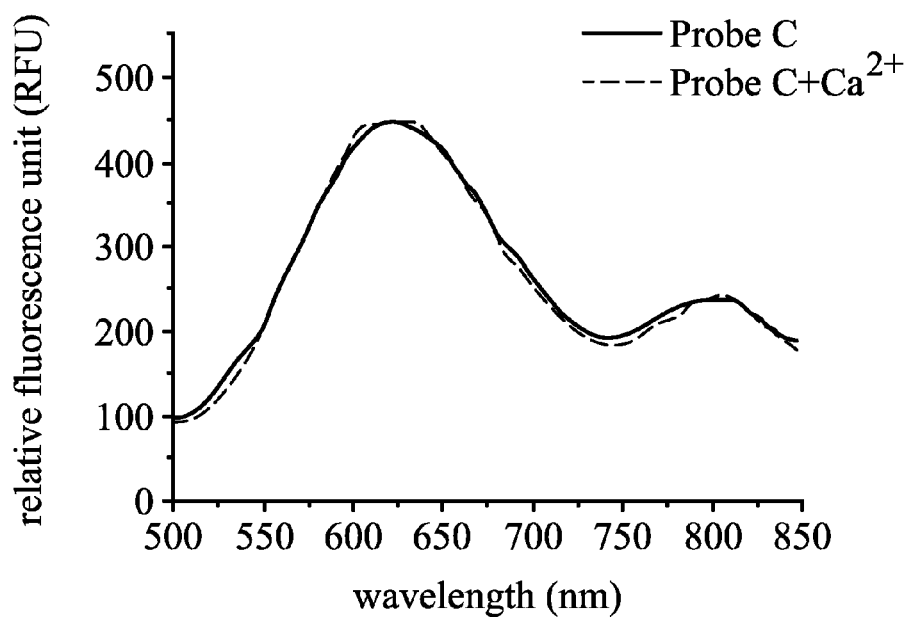

Probes A, B, and C were mixed with 15 μL of a $Ca^{2+}$ ionic solution (100 μM) for 10 minutes to form respective mixtures. The fluorescence spectra of Probes A, B, and C before and after being mixed with the $Ca^{2+}$ ionic solution were compared as shown in FIGS. 13A, 13B, and 13C.

Example 7

Figure 14A:
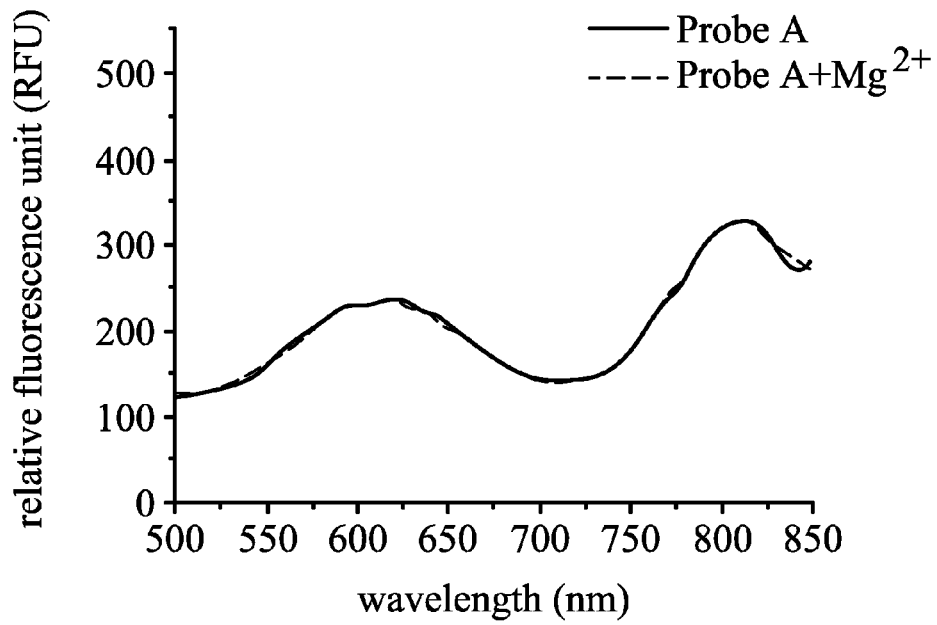
FIGS. 14A, 14B, and 14C show comparisons of fluorescence spectra of Probes A, B, and C before and after being mixed with a $Mg^{2+}$ ionic solution in one embodiment of the disclosure.
Figure 14B:
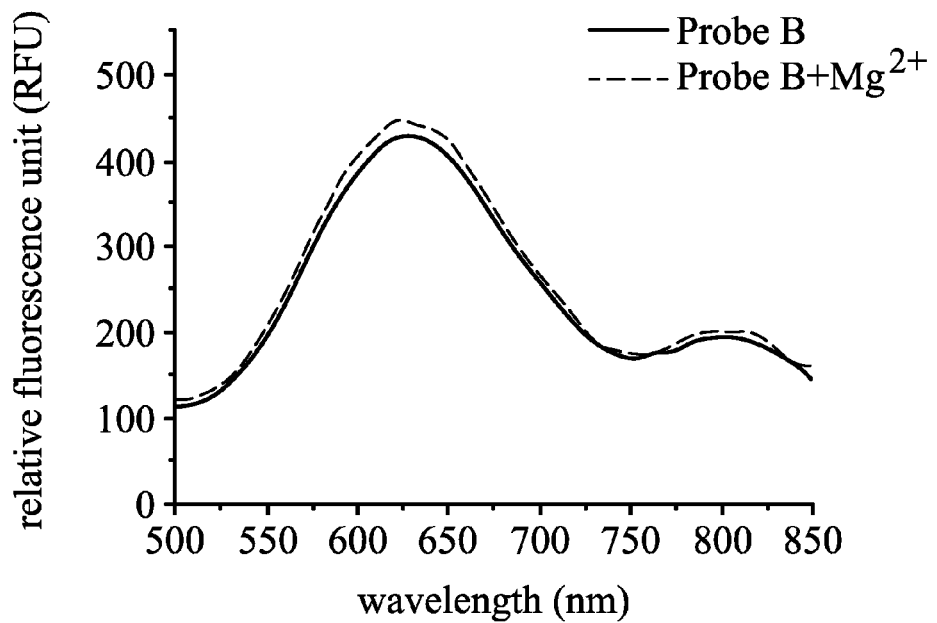
Figure 14C:
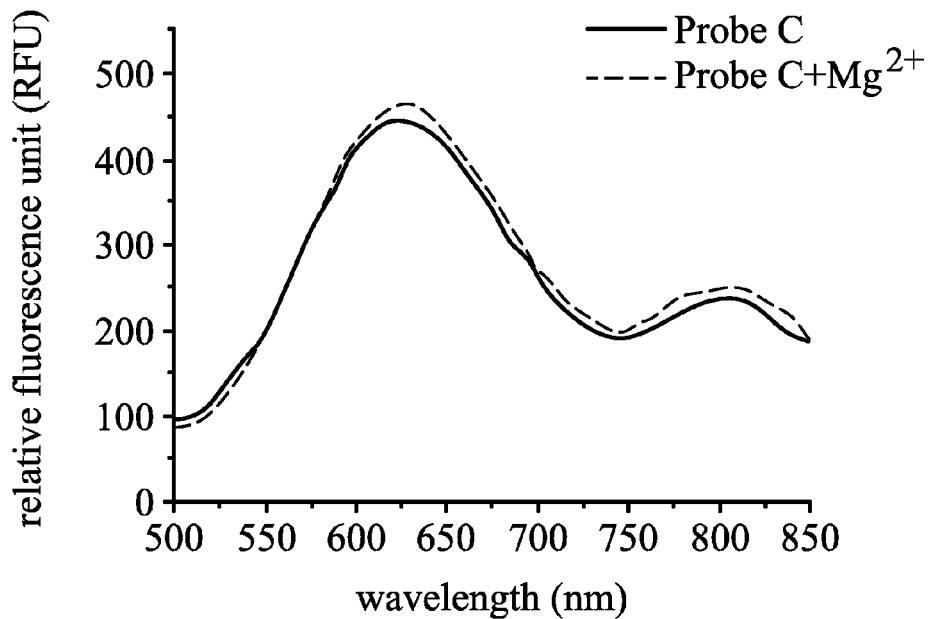

Probes A, B, and C were mixed with 15 μL of a $Mg^{2+}$ ionic solution (100 μM) for 10 minutes to form respective mixtures. The fluorescence spectra of Probes A, B, and C before and after being mixed with the $Mg^{2+}$ ionic solution were compared as shown in FIGS. 14A, 14B, and 14C.

Example 8

Figure 15A:
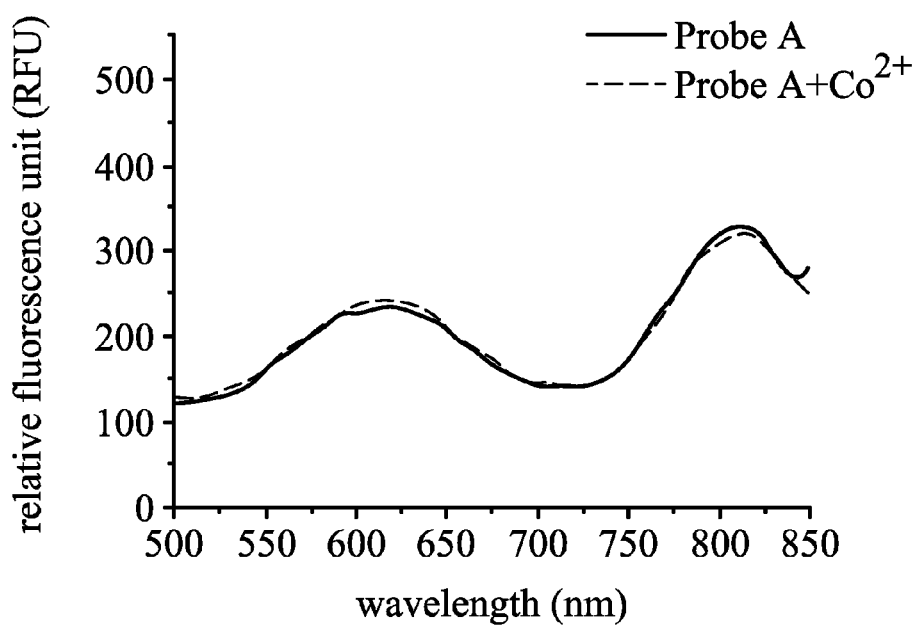
FIGS. 15A, 15B, and 15C show comparisons of fluorescence spectra of Probes A, B, and C before and after being mixed with a $Co^{2+}$ ionic solution in one embodiment of the disclosure.
Figure 15B:
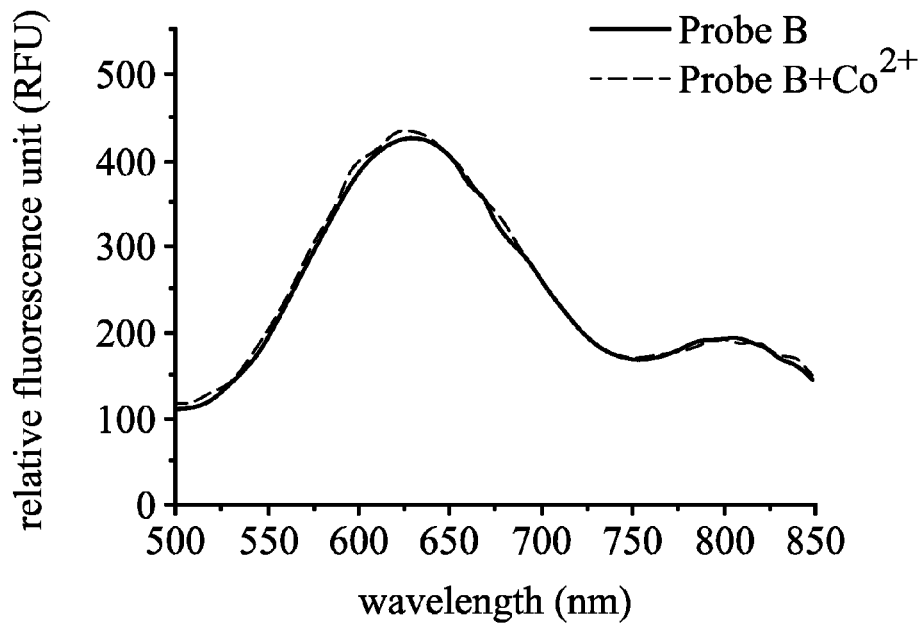
Figure 15C:
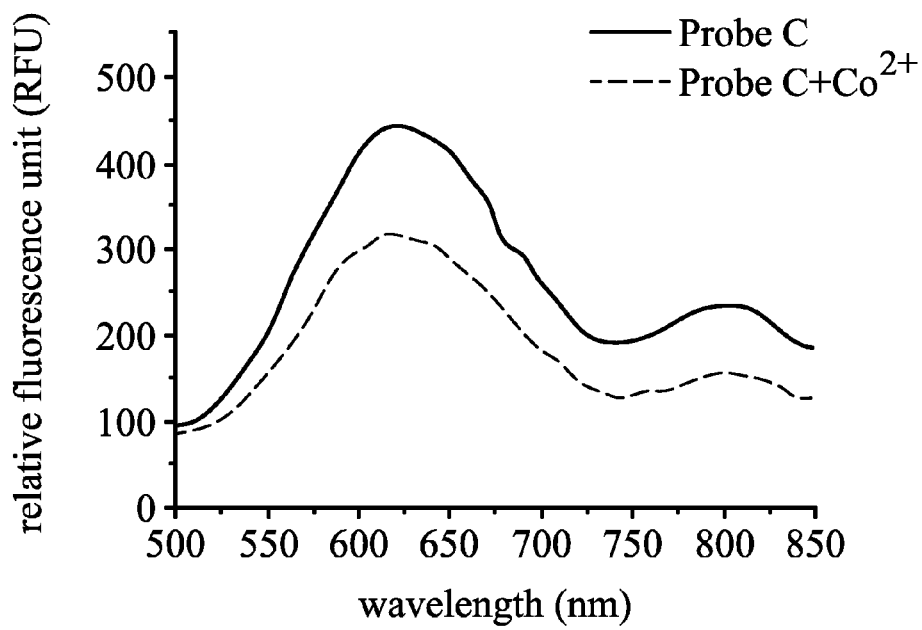

Probes A, B, and C were mixed with 15 μL of a $Co^{2+}$ ionic solution (100 μM) for 10 minutes to form respective mixtures. The fluorescence spectra of Probes A, B, and C before and after being mixed with the $Co^{2+}$ ionic solution were compared as shown in FIGS. 15A, 15B, and 15C.

Example 9

Figure 16A:
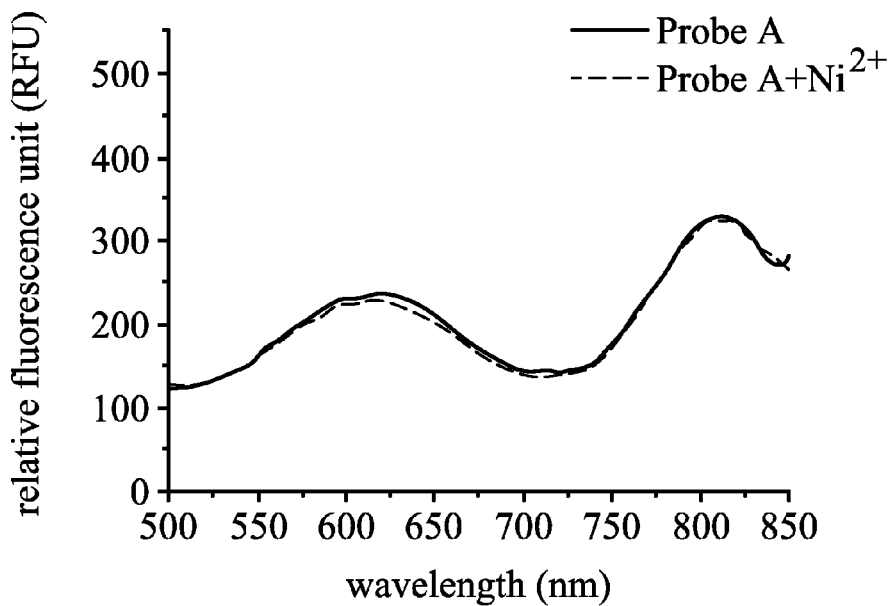
FIGS. 16A, 16B, and 16C show comparisons of fluorescence spectra of Probes A, B, and C before and after being mixed with a $Ni^{2+}$ ionic solution in one embodiment of the disclosure.
Figure 16B:
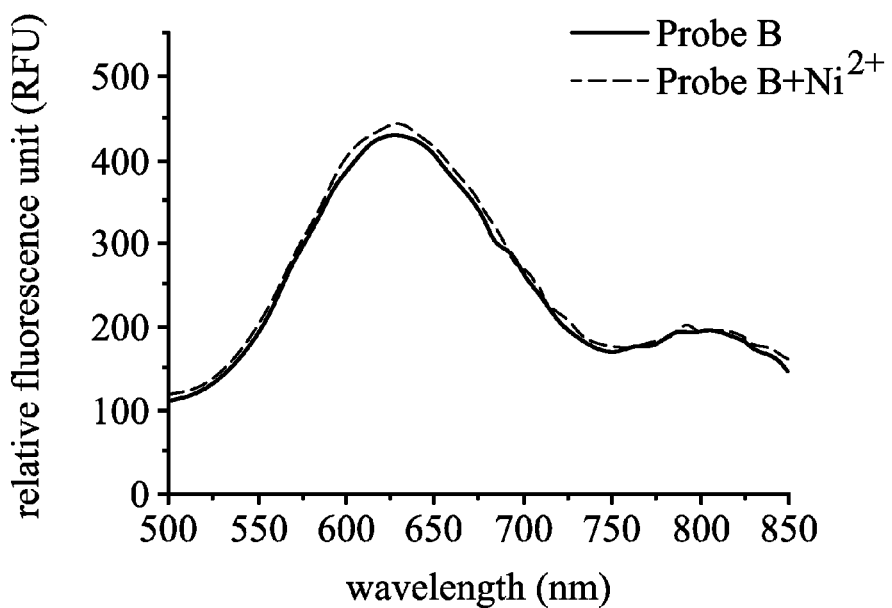
Figure 16C:
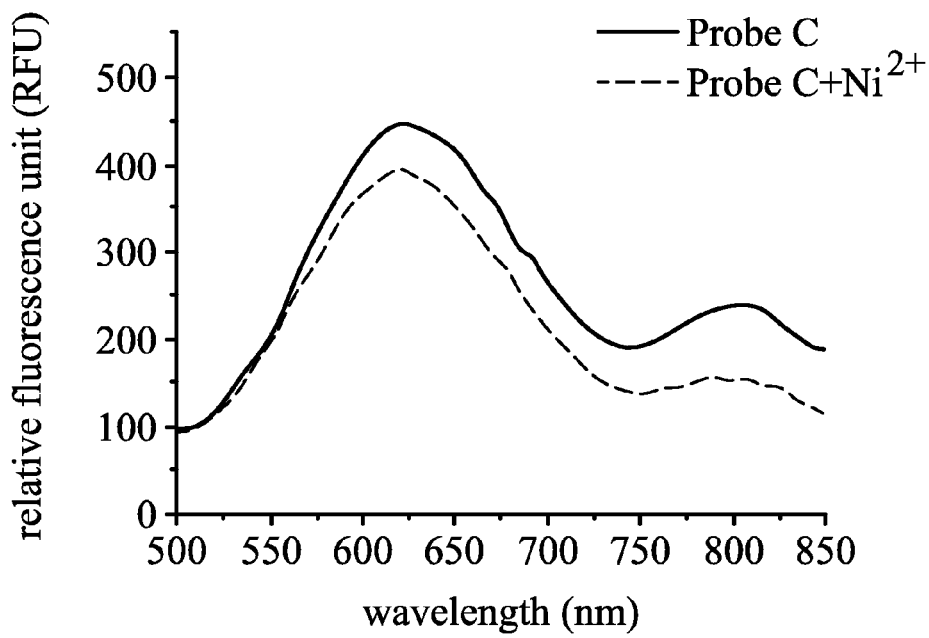

Probes A, B, and C were mixed with 15 μL of a $Ni^{2+}$ ionic solution (100 μM) for 10 minutes to form respective mixtures. The fluorescence spectra of Probes A, B, and C before and after being mixed with the $Ni^{2+}$ ionic solution were compared as shown in FIGS. 16A, 16B, and 16C.

Example 10

Figure 17A:
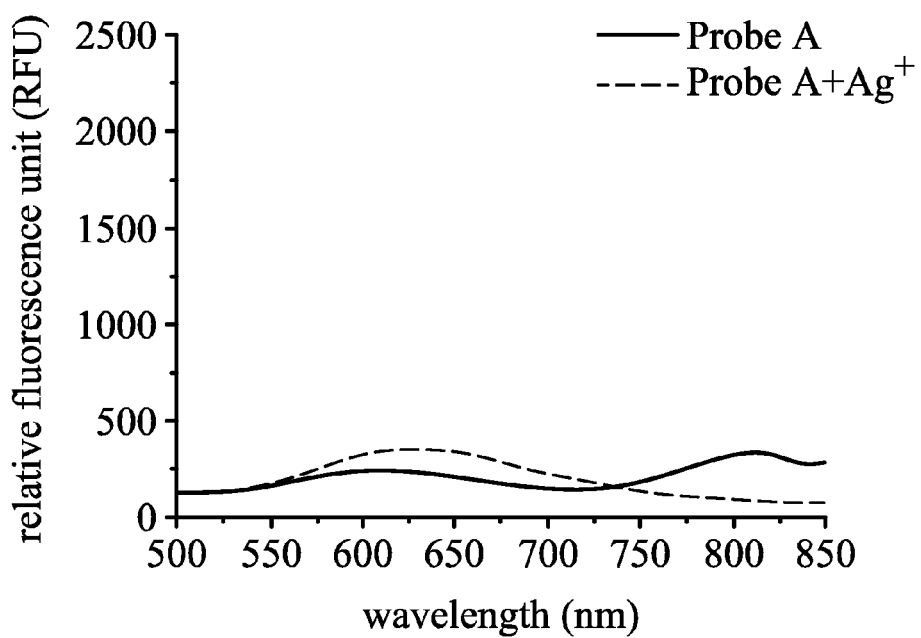
FIGS. 17A, 17B, and 17C show comparisons of fluorescence spectra of Probes A, B, and C before and after being mixed with an $Ag^{+}$ ionic solution in one embodiment of the disclosure.
Figure 17B:
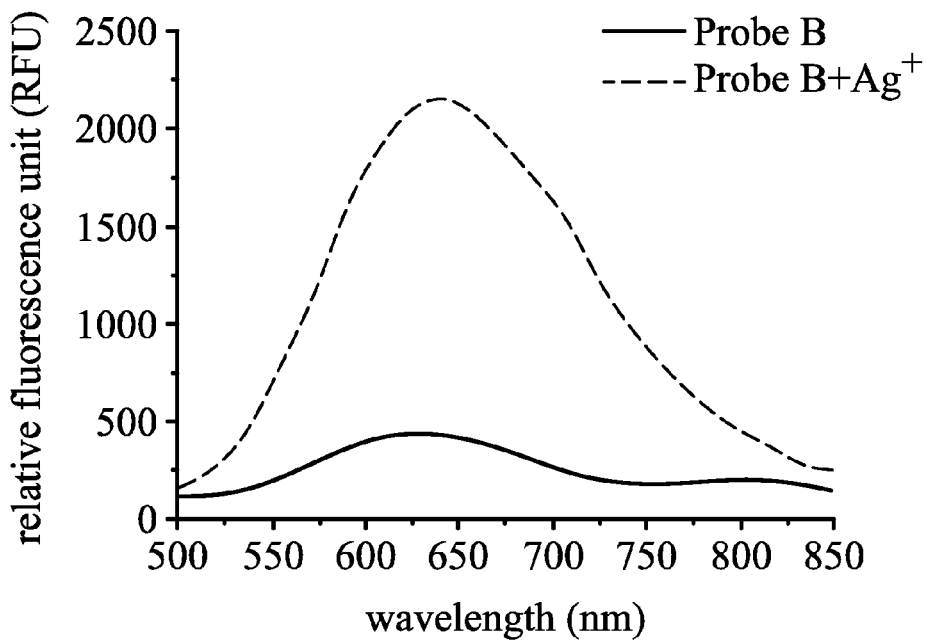
Figure 17C:
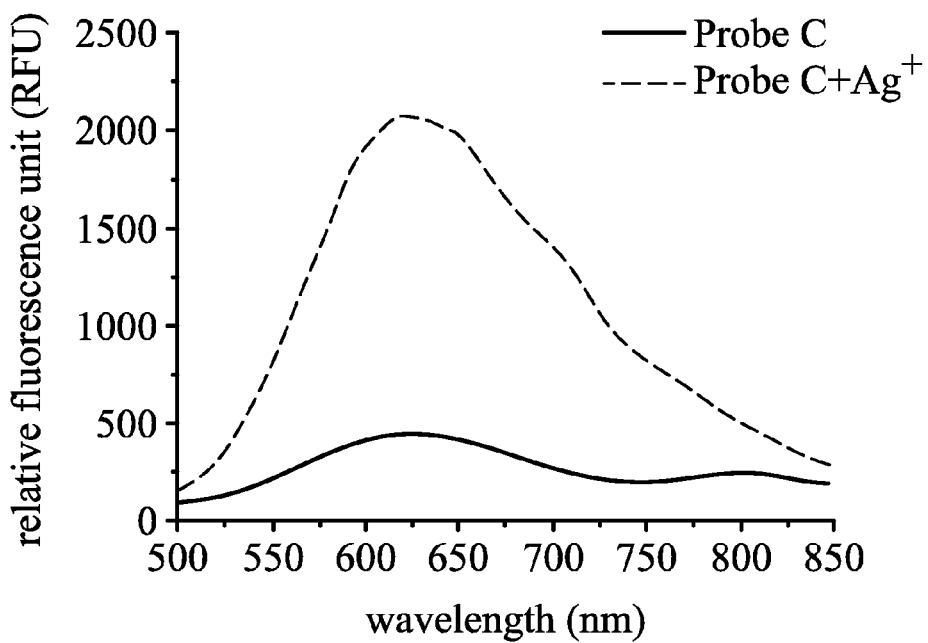

Probes A, B, and C were mixed with 15 μL of a $Ag^{+}$ ionic solution (100 μM) for 10 minutes to form respective mixtures. The fluorescence spectra of Probes A, B, and C before and after being mixed with the $Ag^{+}$ ionic solution were compared as shown in FIGS. 17A, 17B, and 17C.

Example 11

Figure 18A:
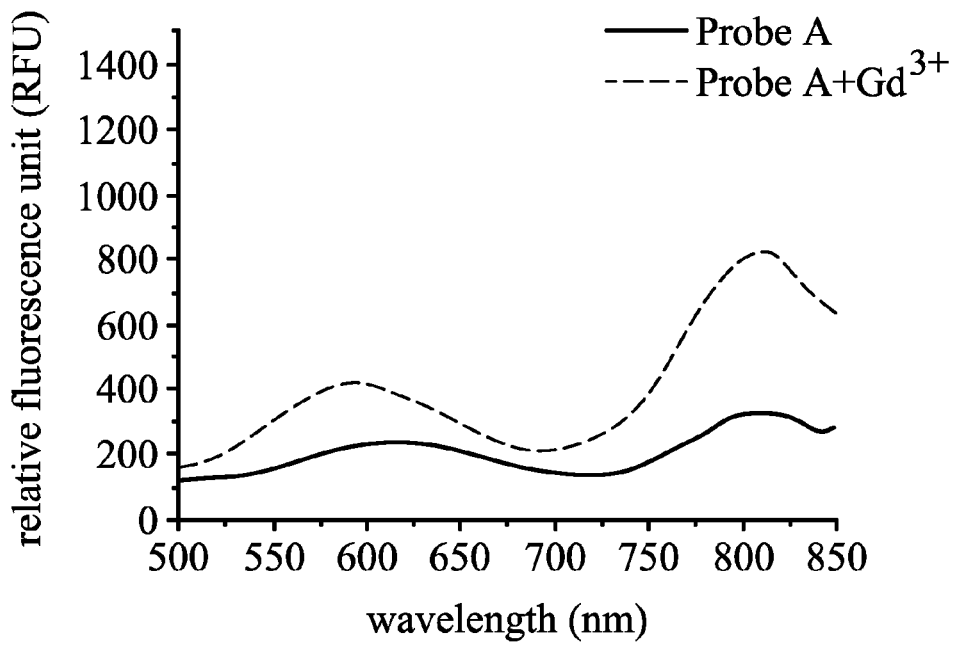
FIGS. 18A, 18B, and 18C show comparisons of fluorescence spectra of Probes A, B, and C before and after being mixed with a $Gd^{3+}$ ionic solution in one embodiment of the disclosure.
Figure 18B:
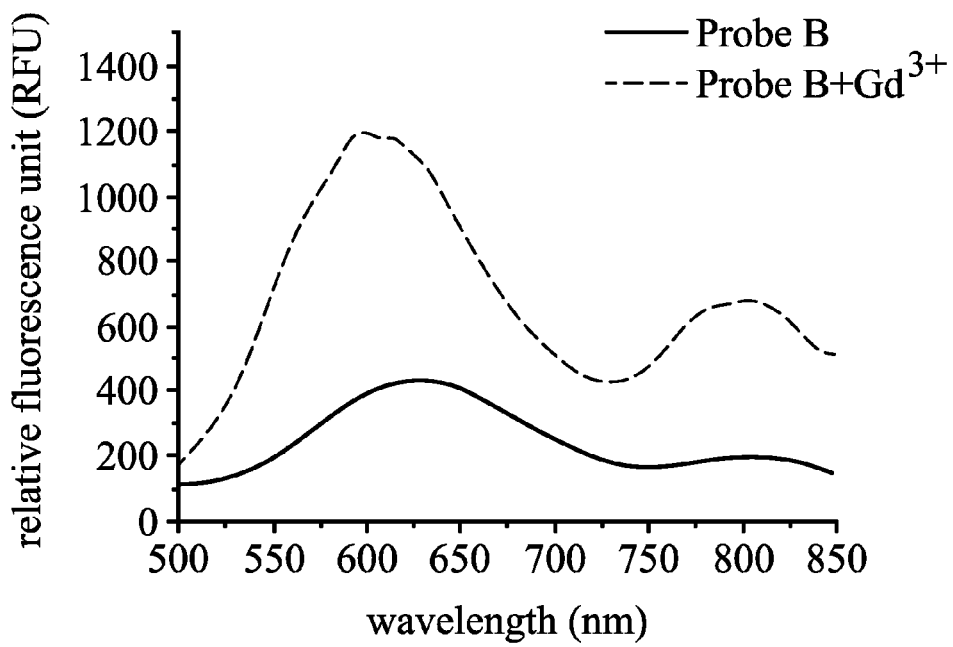
Figure 18C:
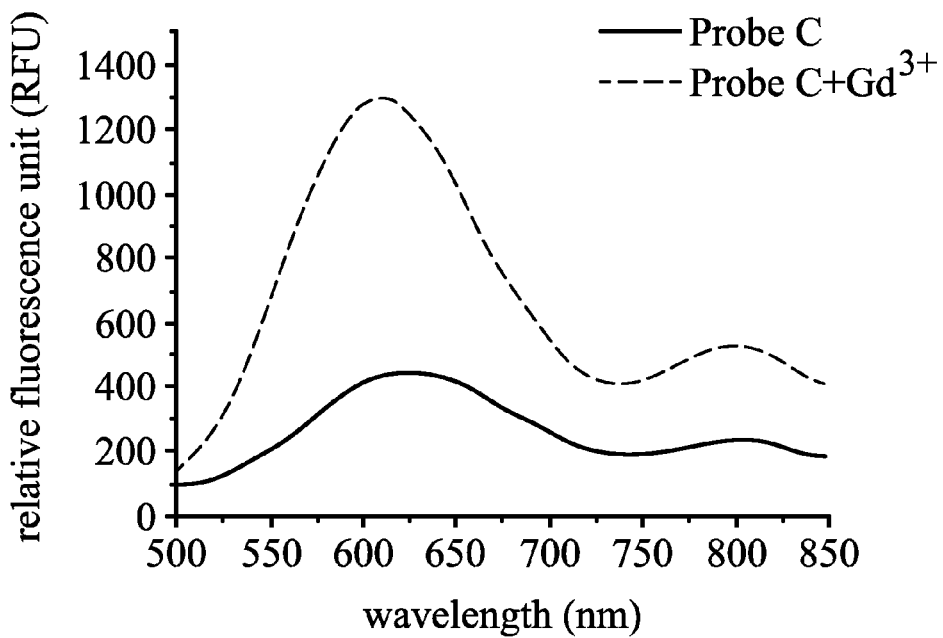

Probes A, B, and C were mixed with 15 μL of a $Gd^{3+}$ ionic solution (100 μM) for 10 minutes to form respective mixtures. The fluorescence spectra of Probes A, B, and C before and after being mixed with the $Gd^{3+}$ ionic solution were compared as shown in FIGS. 18A, 18B, and 18C.

Example 12

Figure 19A:
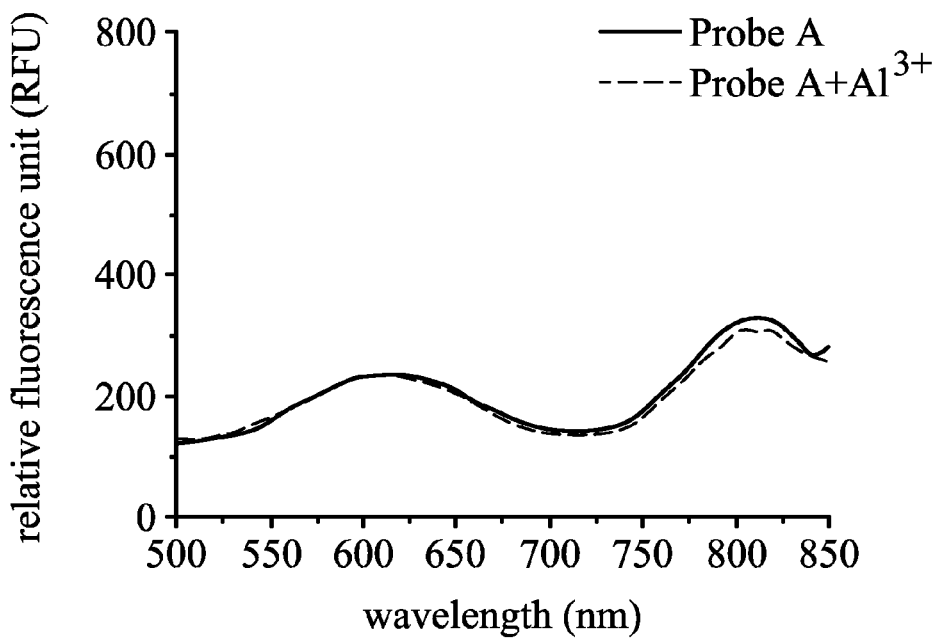
FIGS. 19A, 19B, and 19C show comparisons of fluorescence spectra of Probes A, B, and C before and after being mixed with an $Al^{3+}$ ionic solution in one embodiment of the disclosure.
Figure 19B:
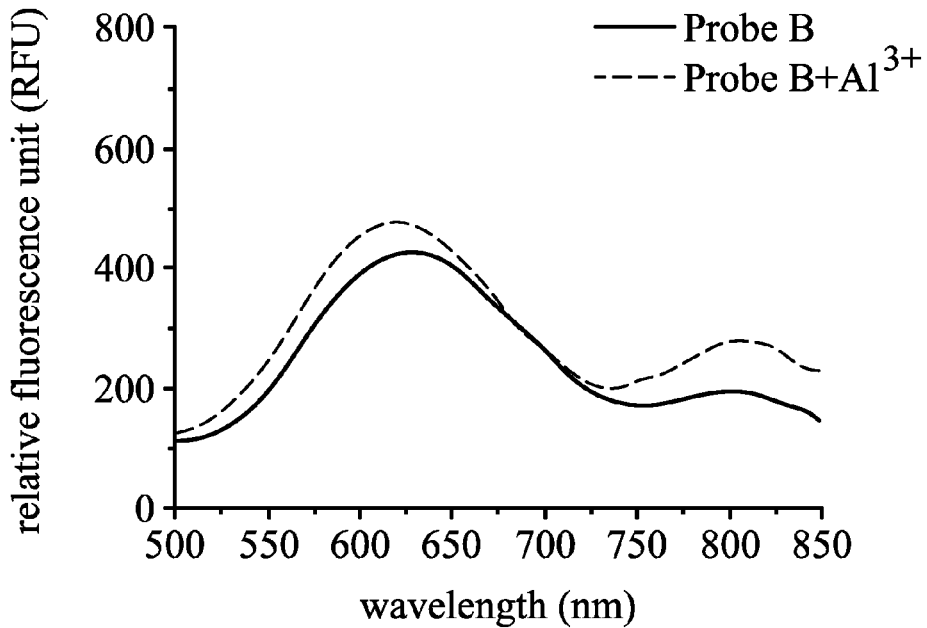
Figure 19C:
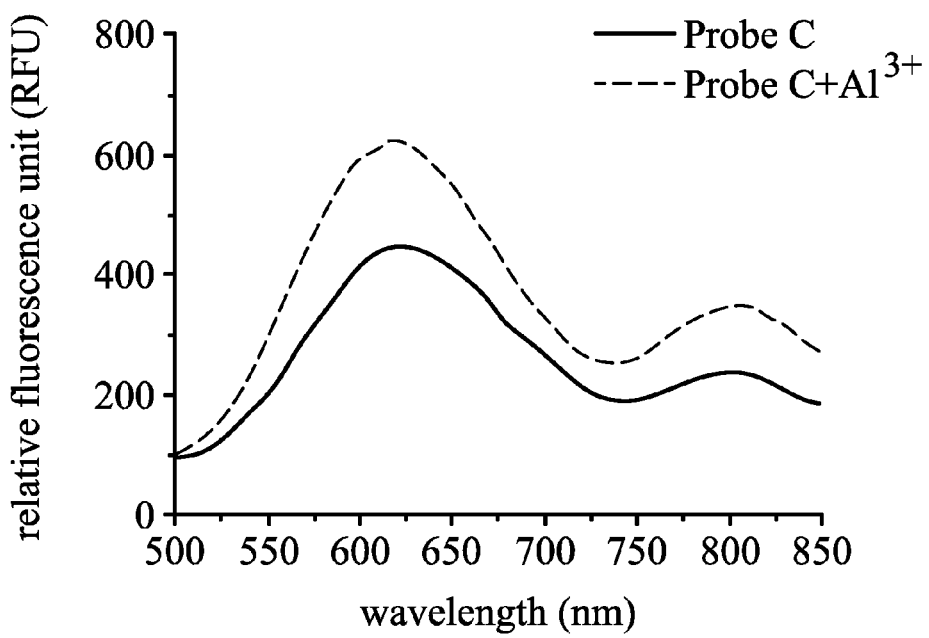

Probes A, B, and C were mixed with 15 μL of an $Al^{3+}$ ionic solution (100 μM) for 10 minutes to form respective mixtures. The fluorescence spectra of Probes A, B, and C before and after being mixed with the $Al^{3+}$ ionic solution were compared as shown in FIGS. 19A, 19B, and 19C.

Example 13

Figure 20A:
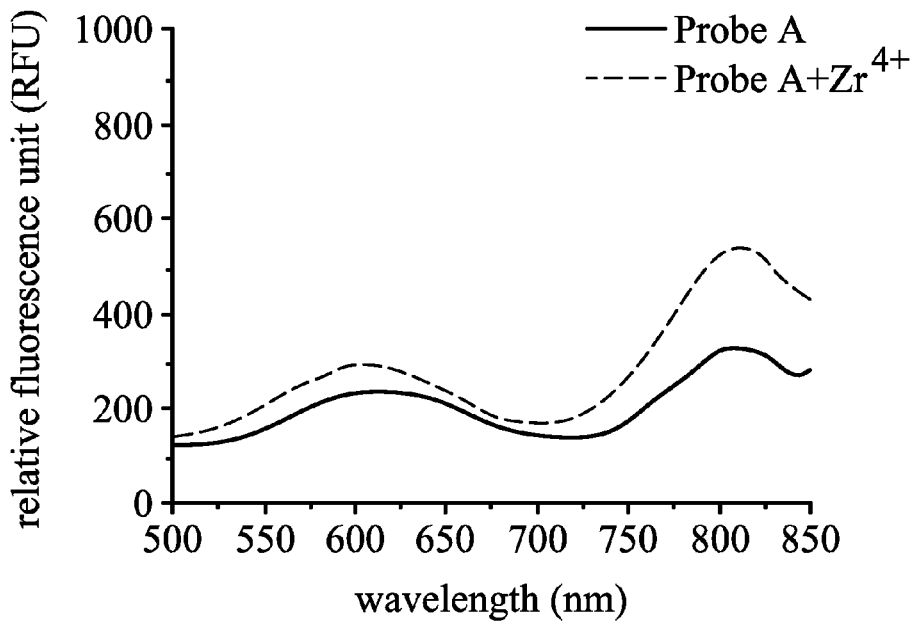
FIGS. 20A, 20B, and 20C show comparisons of fluorescence spectra of Probes A, B, and C before and after being mixed with a $Zr^{4+}$ ionic solution in one embodiment of the disclosure.
Figure 20B:
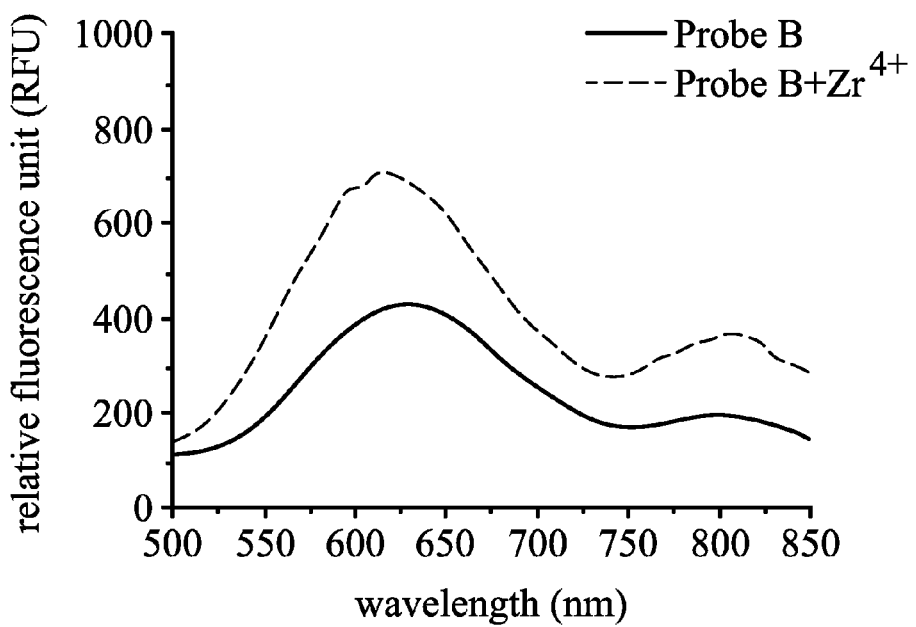
Figure 20C:
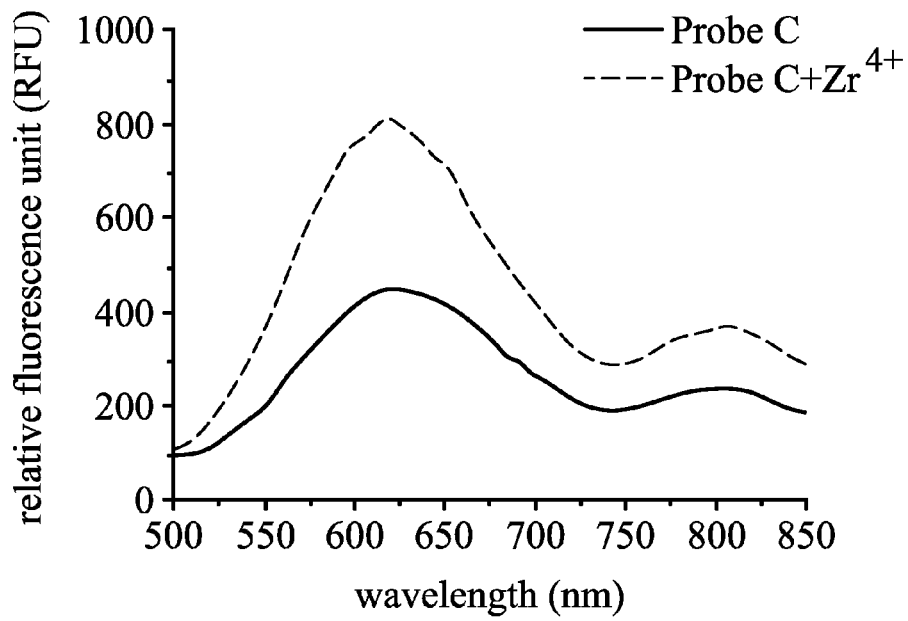

Probes A, B, and C were mixed with 15 μL of a $Zr^{4+}$ ionic solution (100 μM) for 10 minutes to form respective mixtures. The fluorescence spectra of Probes A, B, and C before and after being mixed with the $Zr^{4+}$ ionic solution were compared as shown in FIGS. 20A, 20B, and 20C.

Example 14

Figure 21A:
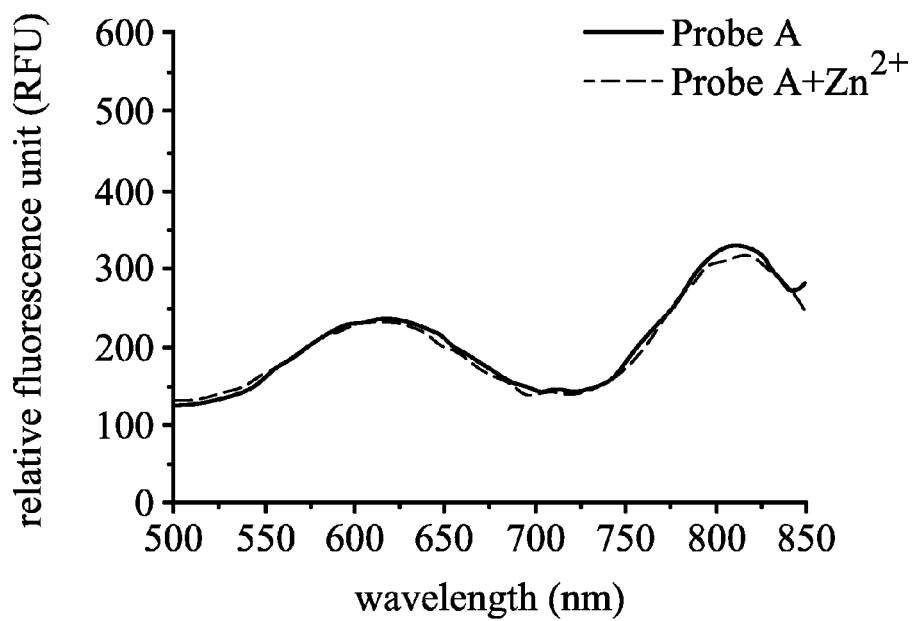
FIGS. 21A, 21B, and 21C show comparisons of fluorescence spectra of Probes A, B, and C before and after being mixed with a $Zn^{2+}$ ionic solution in one embodiment of the disclosure.
Figure 21B:
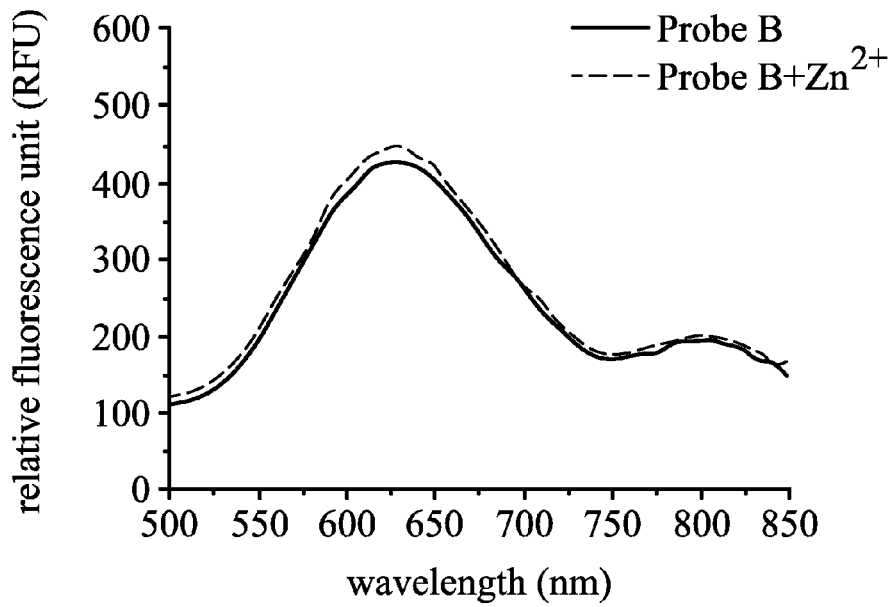
Figure 21C:
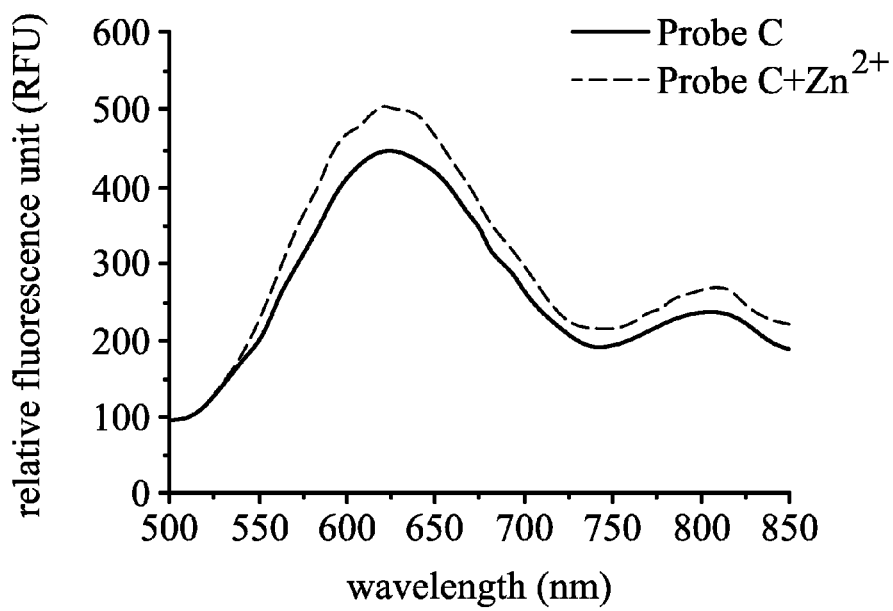

Probes A, B, and C were mixed with 15 μL of a $Zn^{2+}$ ionic solution (100 μM) for 10 minutes to form mixtures, respectively. The fluorescence spectra of Probes A, B, and C before and after being mixed with the $Zn^{2+}$ ionic solution were compared as shown in FIGS. 21A, 21B, and 21C.

Example 15

Figure 22A:
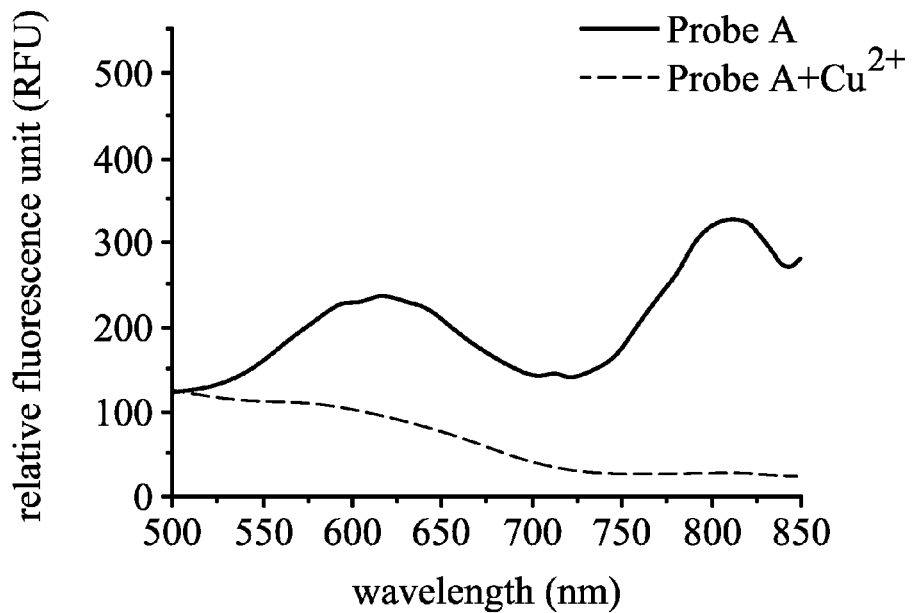
FIGS. 22A, 22B, and 22C show comparisons of fluorescence spectra of Probes A, B, and C before and after being mixed with a $Cu^{2+}$ ionic solution in one embodiment of the disclosure.
Figure 22B:
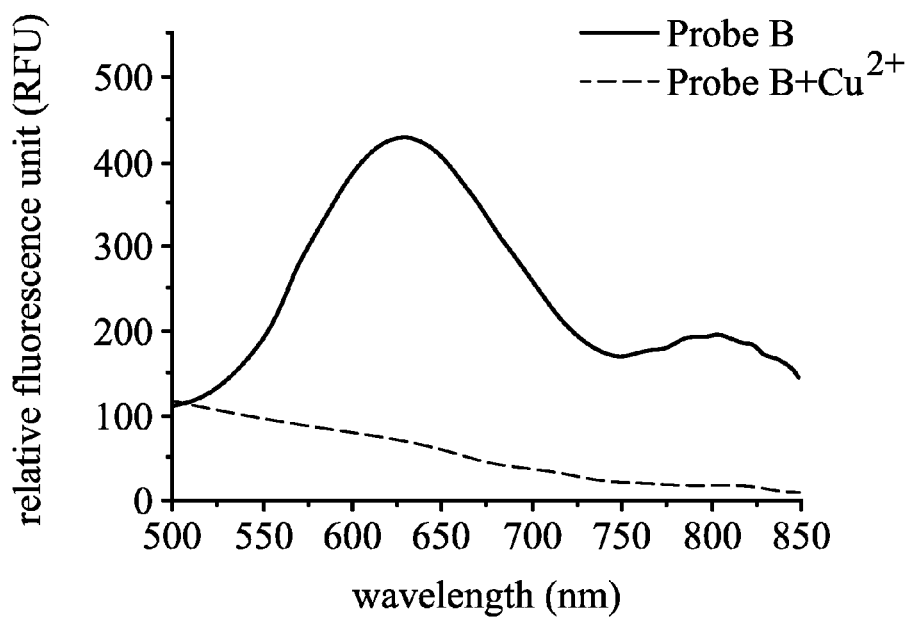
Figure 22C:
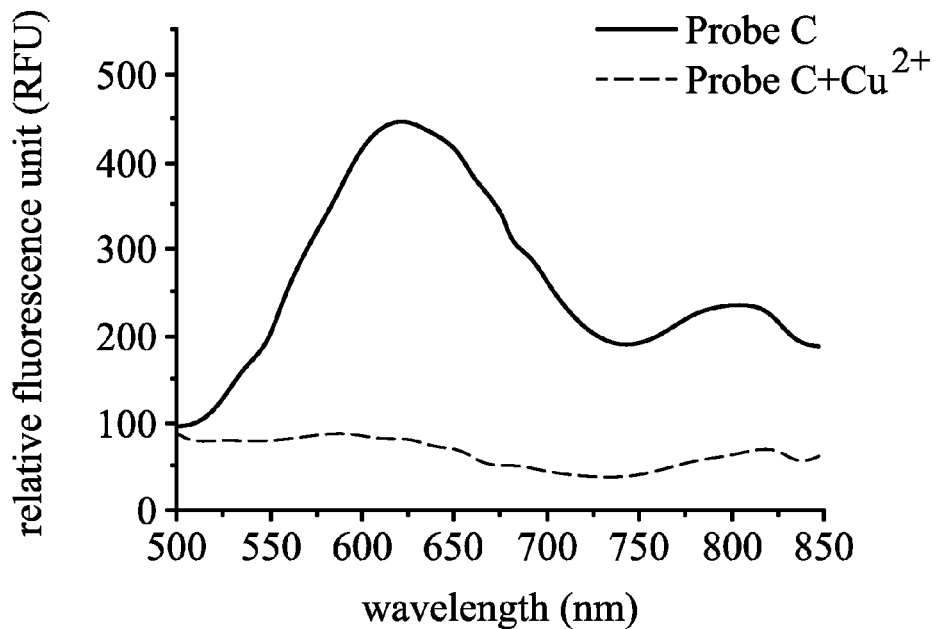

Probes A, B, and C were mixed with 15 μL of a $Cu^{2+}$ ionic solution (100 μM) for 10 minutes to form respective mixtures. The fluorescence spectra of Probes A, B, and C before and after being mixed with the $Cu^{2+}$ ionic solution were compared as shown in FIGS. 22A, 22B, and 22C.

Example 16

Figure 23A:
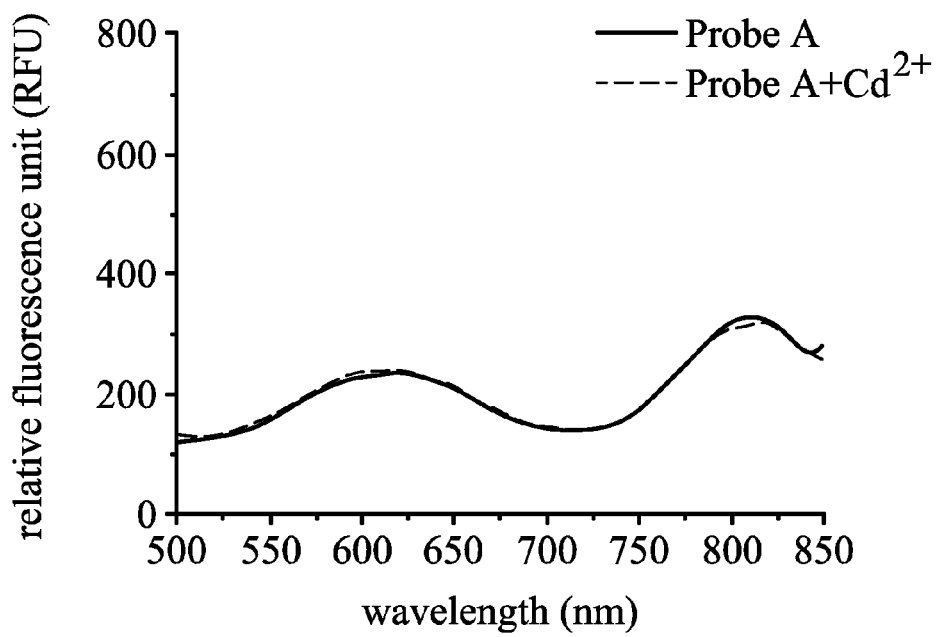
FIGS. 23A, 23B, and 23C show comparisons of fluorescence spectra of Probes A, B, and C before and after being mixed with a $Cd^{2+}$ ionic solution in one embodiment of the disclosure.
Figure 23B:
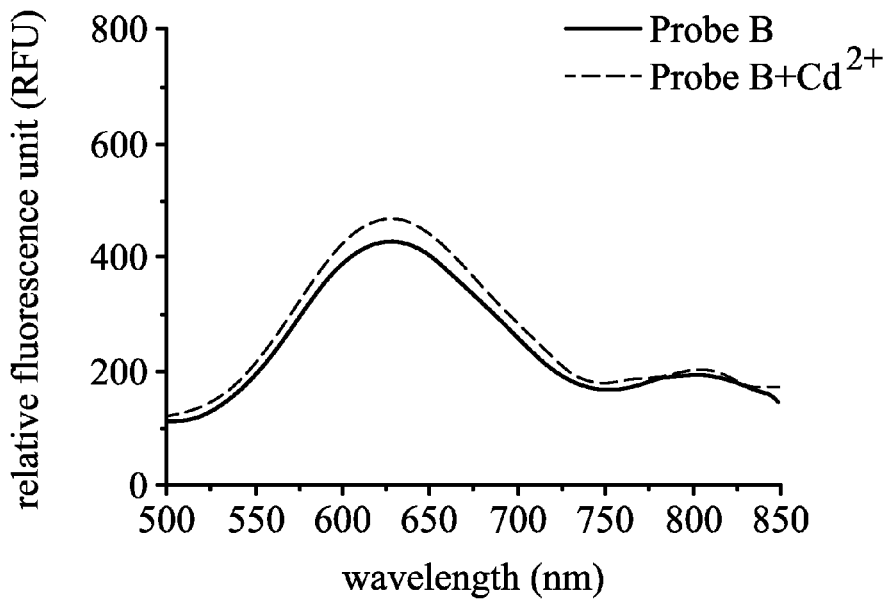
Figure 23C:
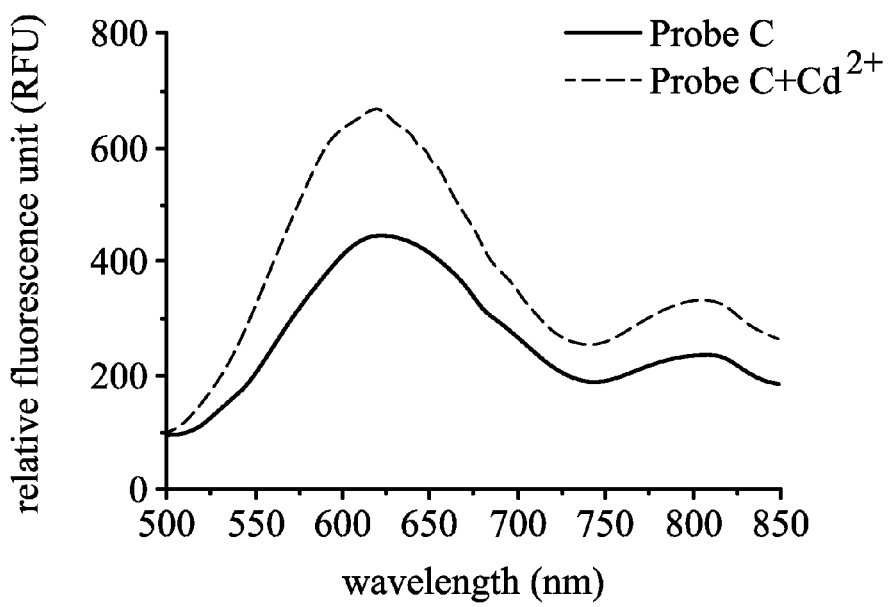

Probes A, B, and C were mixed with 15 μL of a $Cd^{2+}$ ionic solution (100 μM) for 10 minutes to form respective mixtures. The fluorescence spectra of Probes A, B, and C before and after being mixed with the $Cd^{2+}$ ionic solution were compared as shown in FIGS. 23A, 23B, and 23C.

Example 17

Figure 24A:
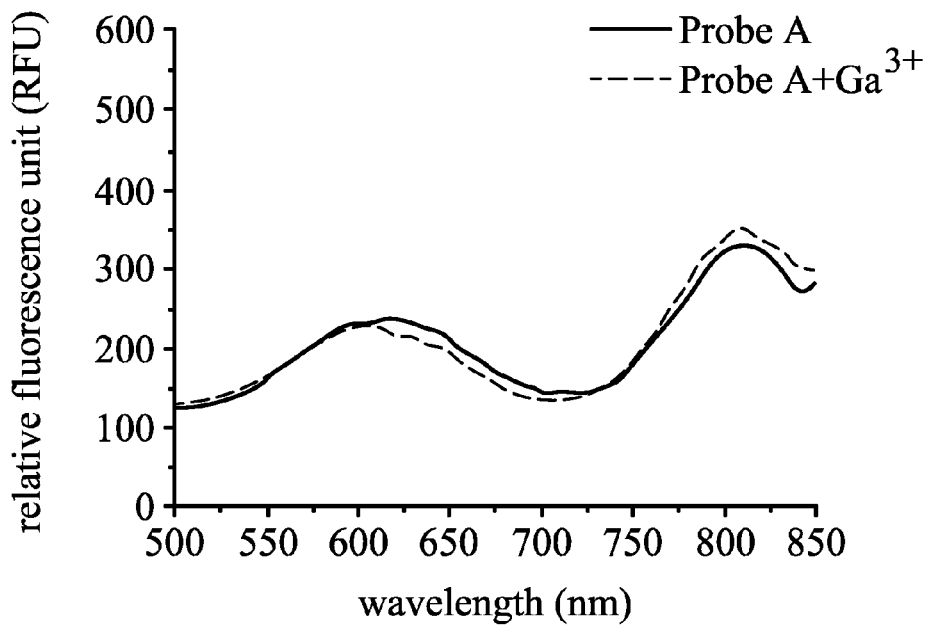
FIGS. 24A, 24B, and 24C show comparisons of fluorescence spectra of Probes A, B, and C before and after being mixed with a $Ga^{3+}$ ionic solution in one embodiment of the disclosure.
Figure 24B:
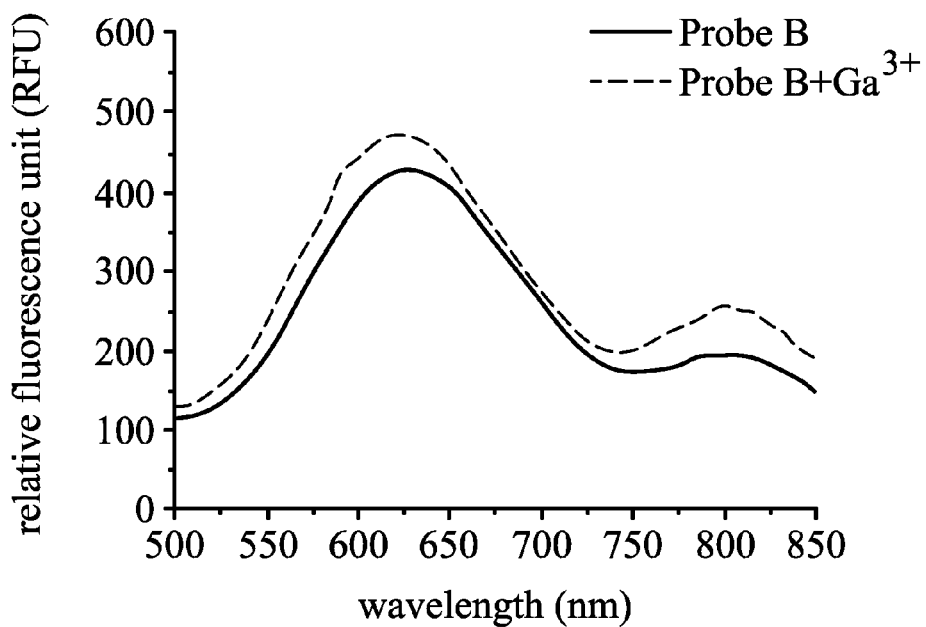
Figure 24C:
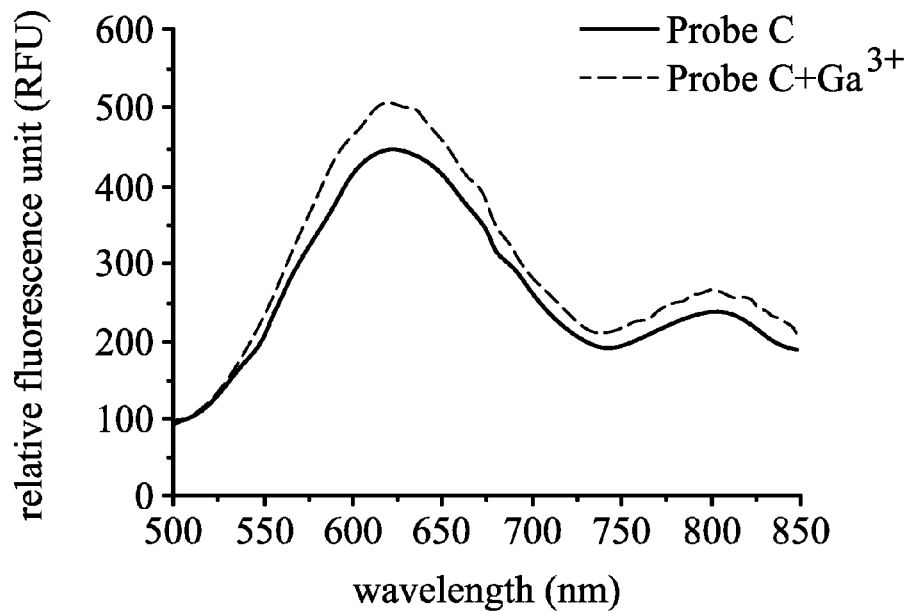

Probes A, B, and C were mixed with 15 μL of a $Ga^{3+}$ ionic solution (100 μM) for 10 minutes to form respective mixtures. The fluorescence spectra of Probes A, B, and C before and after being mixed with the $Ga^{3+}$ ionic solution were compared as shown in FIGS. 24A, 24B, and 24C.

Example 18

Figure 25A:
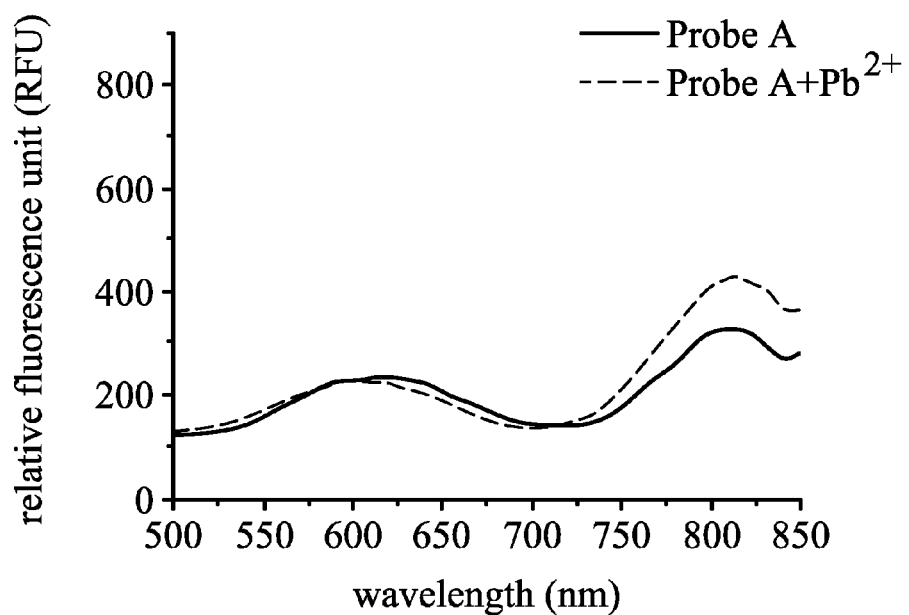
FIGS. 25A, 25B, and 25C show comparisons of fluorescence spectra of Probes A, B, and C before and after being mixed with a $Pb^{2+}$ ionic solution in one embodiment of the disclosure.
Figure 25B:
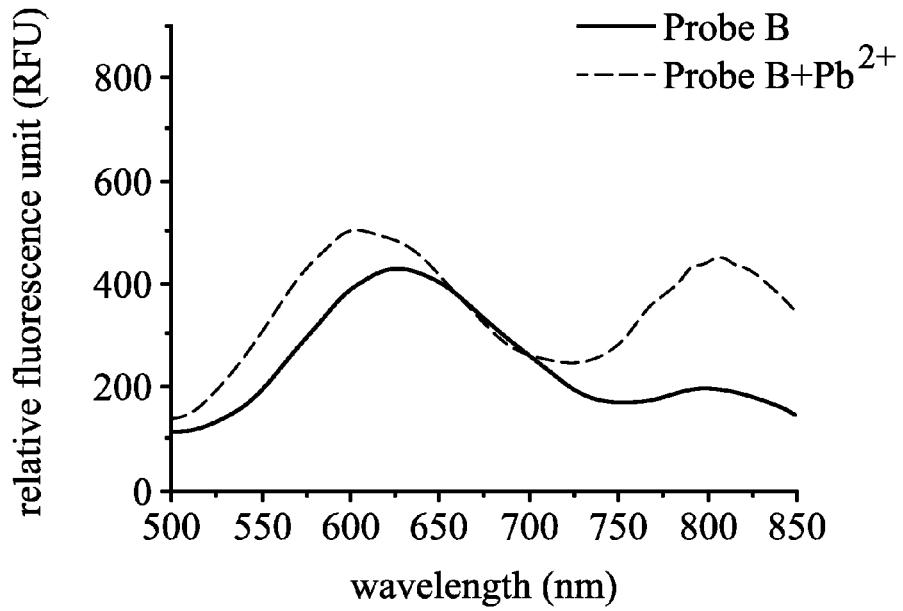
Figure 25C:
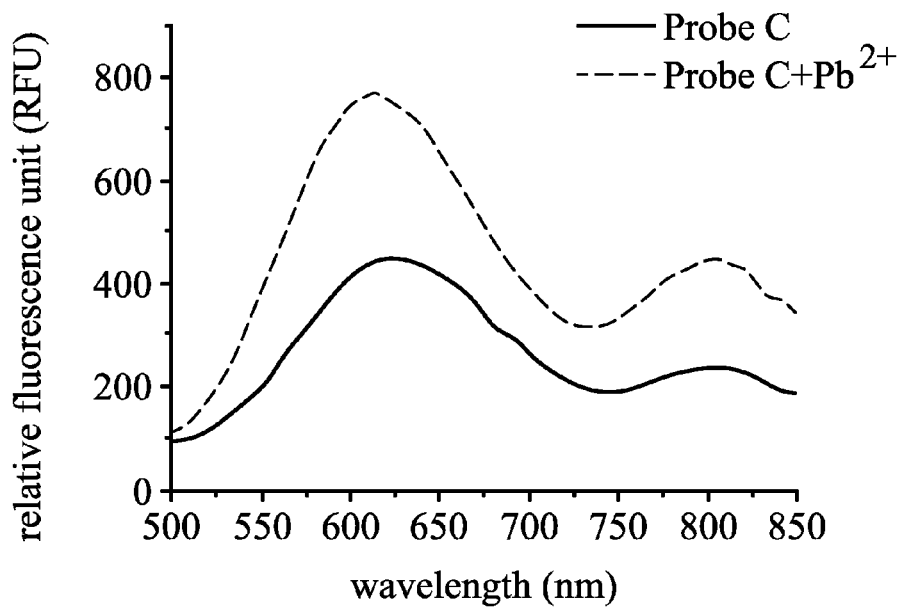

Probes A, B, and C were mixed with 15 μL of a $Pb^{2+}$ ionic solution (100 μM) for 10 minutes to form respective mixtures. The fluorescence spectra of Probes A, B, and C before and after being mixed with the $Pb^{2+}$ ionic solution were compared as shown in FIGS. 25A, 25B, and 25C.

Example 19

Figure 26A:
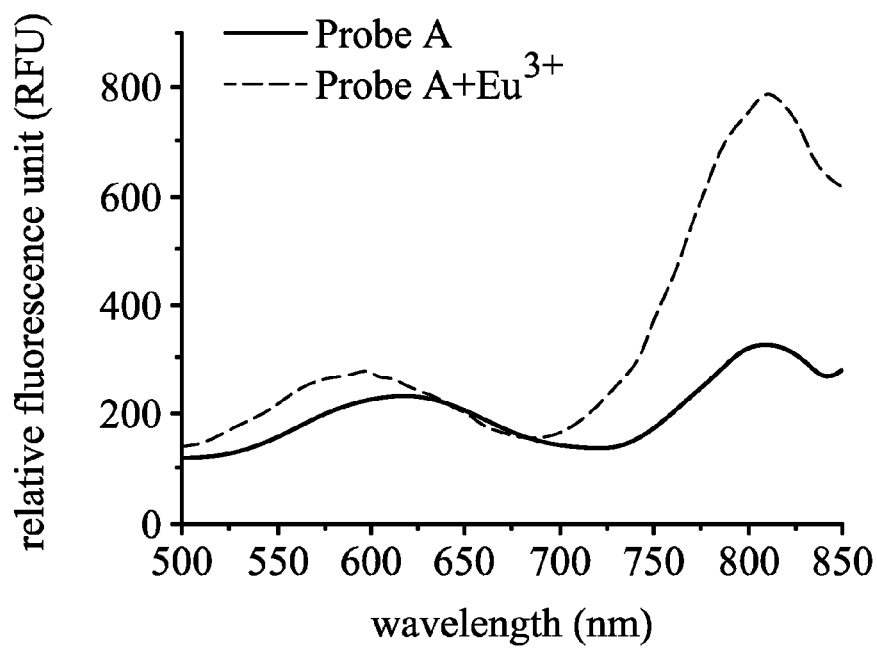
FIGS. 26A, 26B, and 26C show comparisons of fluorescence spectra of Probes A, B, and C before and after being mixed with an $Eu^{3+}$ ionic solution in one embodiment of the disclosure.
Figure 26B:
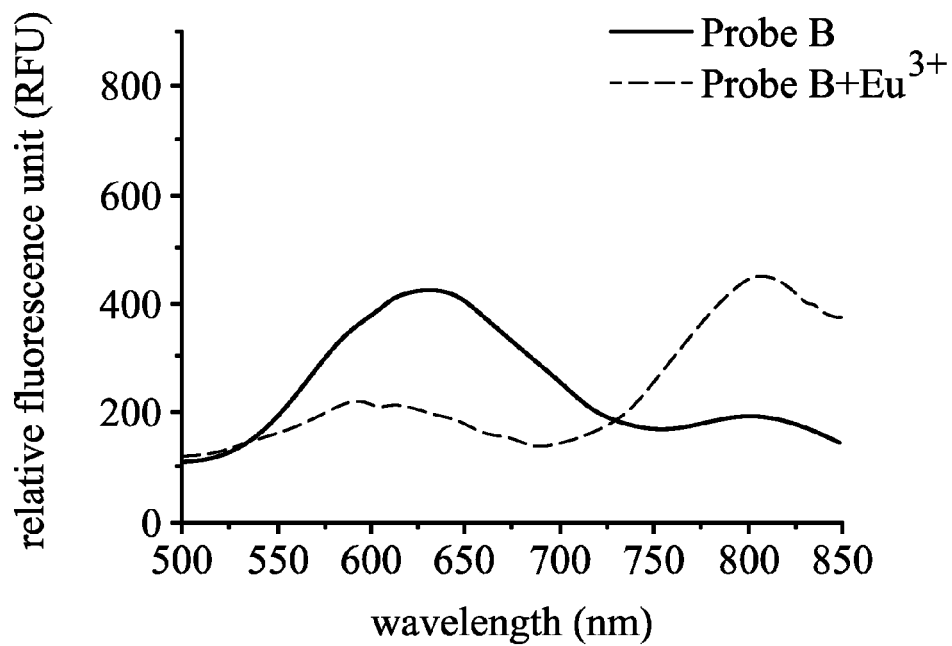
Figure 26C:
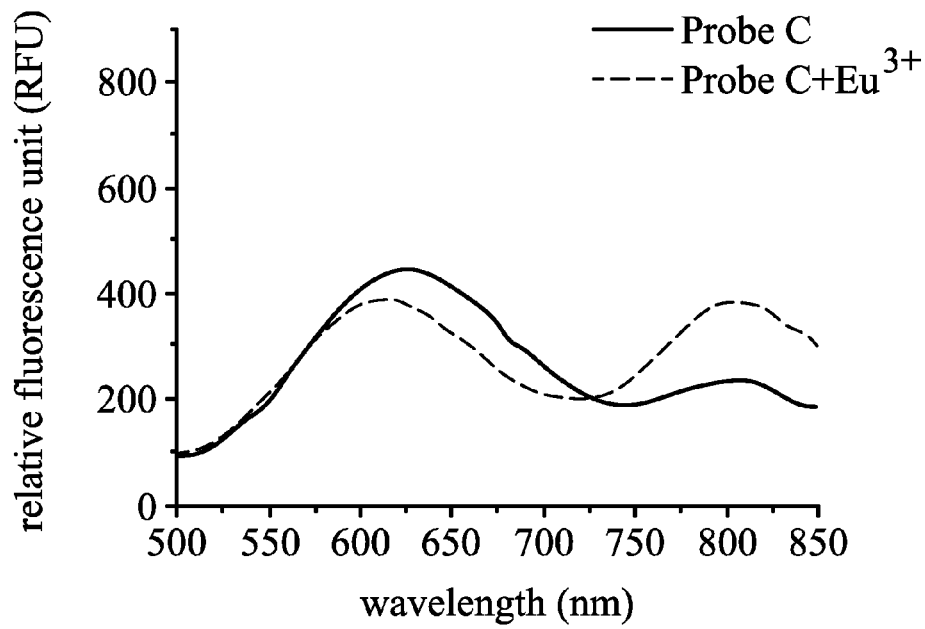

Probes A, B, and C were mixed with 15 μL of an $Eu^{3+}$ ionic solution (100 μM) for 10 minutes to form respective mixtures. The fluorescence spectra of Probes A, B, and C before and after being mixed with the $Eu^{3+}$ ionic solution were compared as shown in FIGS. 26A, 26B, and 26C.

Example 20

Figure 27A:
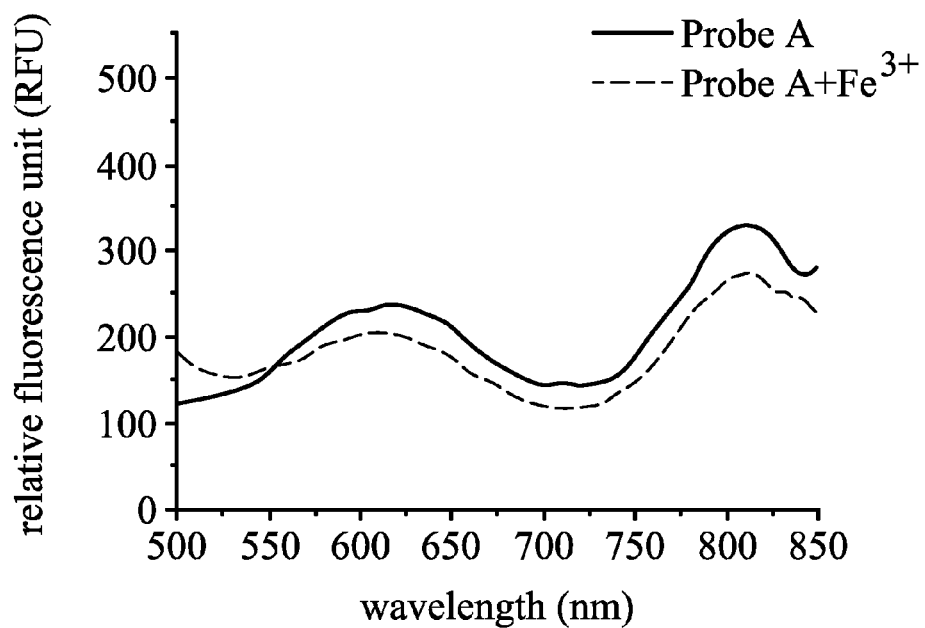
FIGS. 27A, 27B, and 27C show comparisons of fluorescence spectra of Probes A, B, and C before and after being mixed with a $Fe^{3+}$ ionic solution in one embodiment of the disclosure.
Figure 27B:
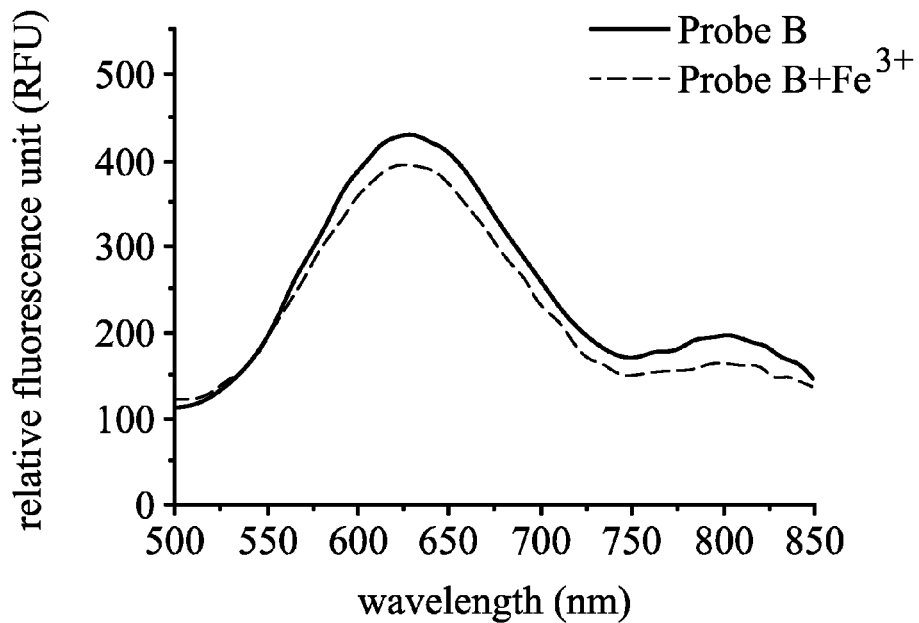
Figure 27C:
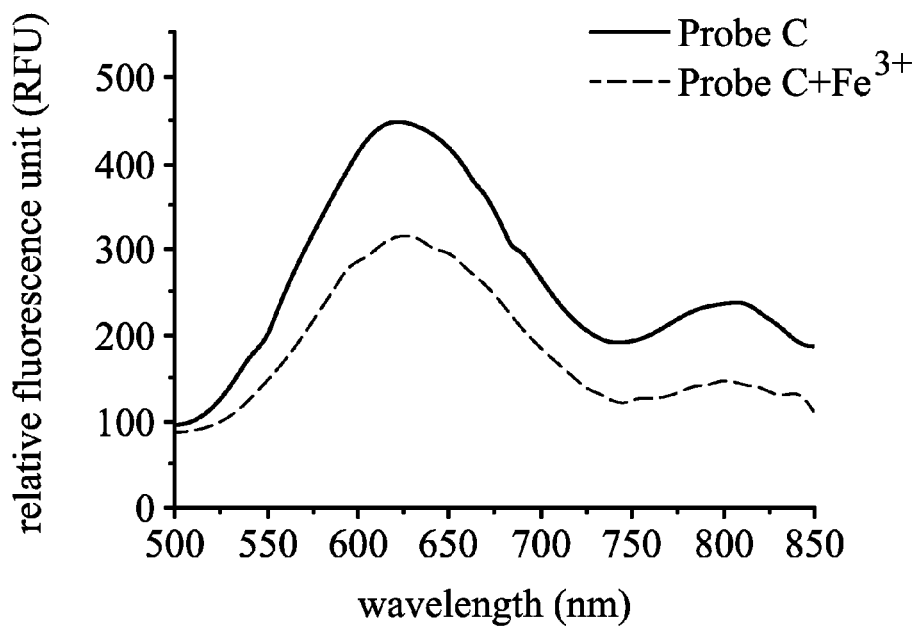

Probes A, B, and C were mixed with 15 μL of a $Fe^{3+}$ ionic solution (100 μM) for 10 minutes to form respective mixtures. The fluorescence spectra of Probes A, B, and C before and after being mixed with the $Fe^{3+}$ ionic solution were compared as shown in FIGS. 27A, 27B, and 27C.

Example 21

Figure 28A:
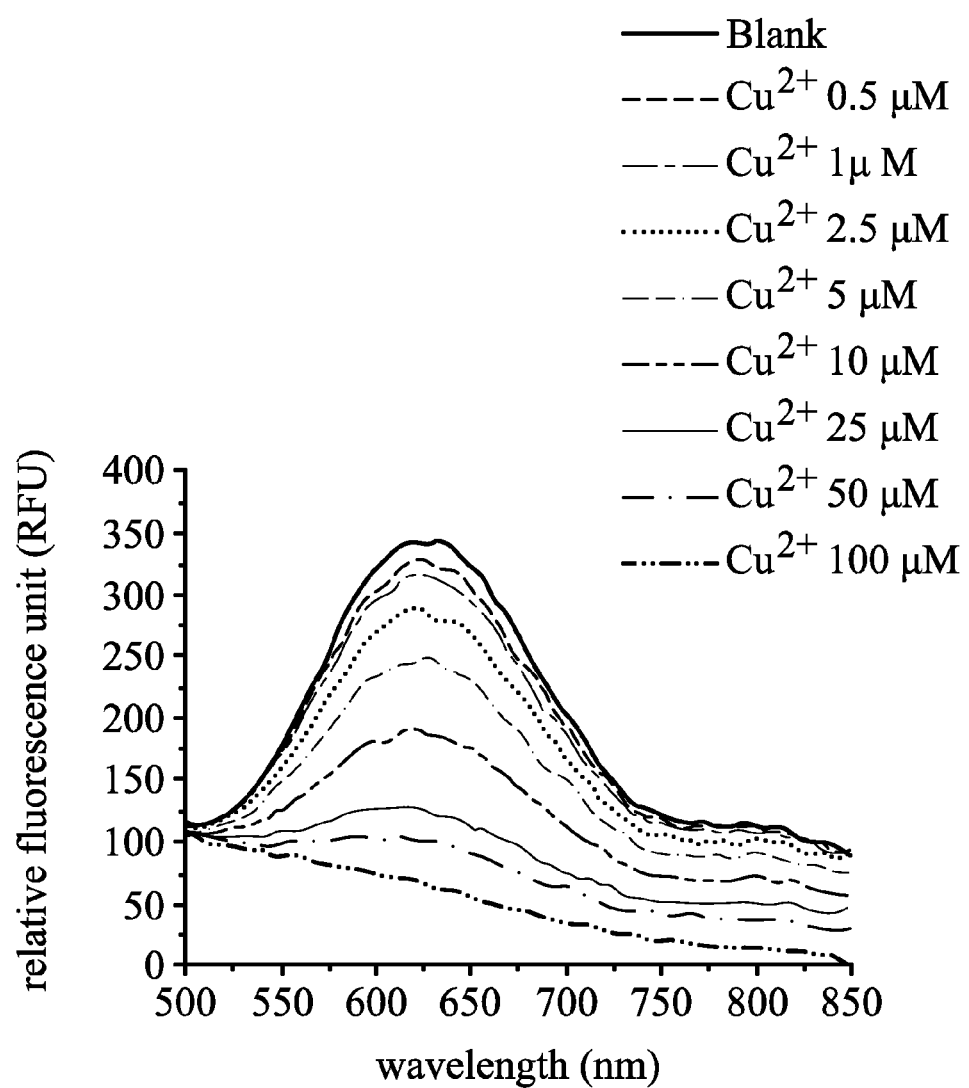
FIGS. 28A and 28B show a qualitative analysis diagram and a quantitative analysis diagram of $Cu^{2+}$ ionic solutions measured by Probe D in one embodiment of the disclosure.
Figure 28B:
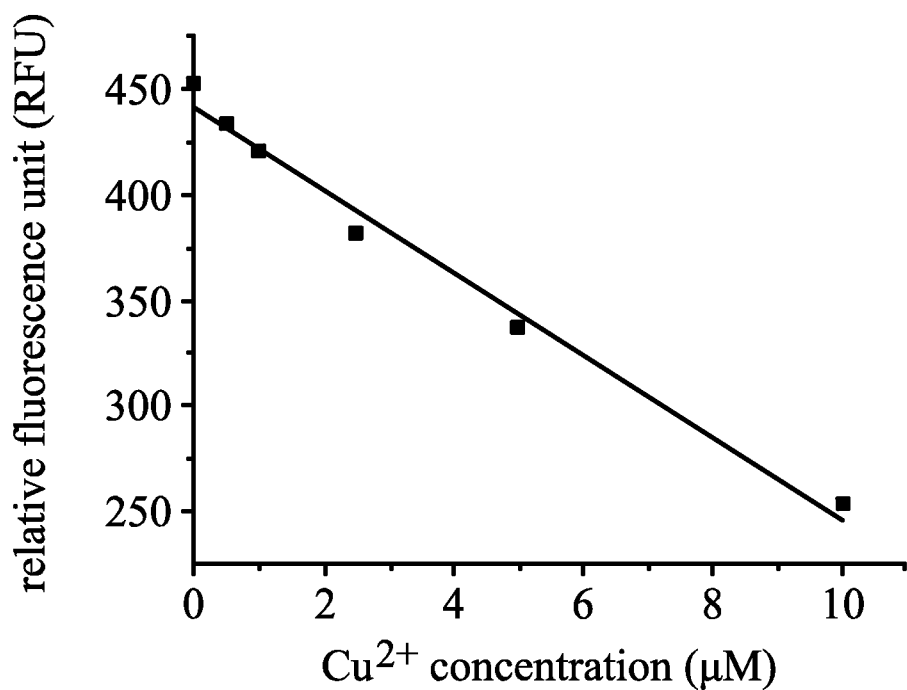

Probe D was mixed with 15 μL of $Cu^{2+}$ ionic solutions of different concentrations (0.5 μM, 1 μM, 2.5 μM, 5 μM, 10 μM, 25 μM, 50 μM, and 100 μM) for 10 minutes to form respective mixtures. The fluorescence spectra of Probe D mixed with the $Cu^{2+}$ ionic solutions of different concentrations were compared as shown in FIG. 28A. The sum of the increase of the fluorescence emission intensity at a wavelength of 630 nm and the decrease of the fluorescence emission intensity at a wavelength of 810 nm of the fluorescence spectra of Probe D mixed with the $Cu^{2+}$ ionic solutions of different concentrations is shown in FIG. 28B. Accordingly, the probe of the disclosure not only qualitatively measured the metal ions in the analytes, but also quantitatively measured the concentration of the metal ions.

Example 22

Figure 2:
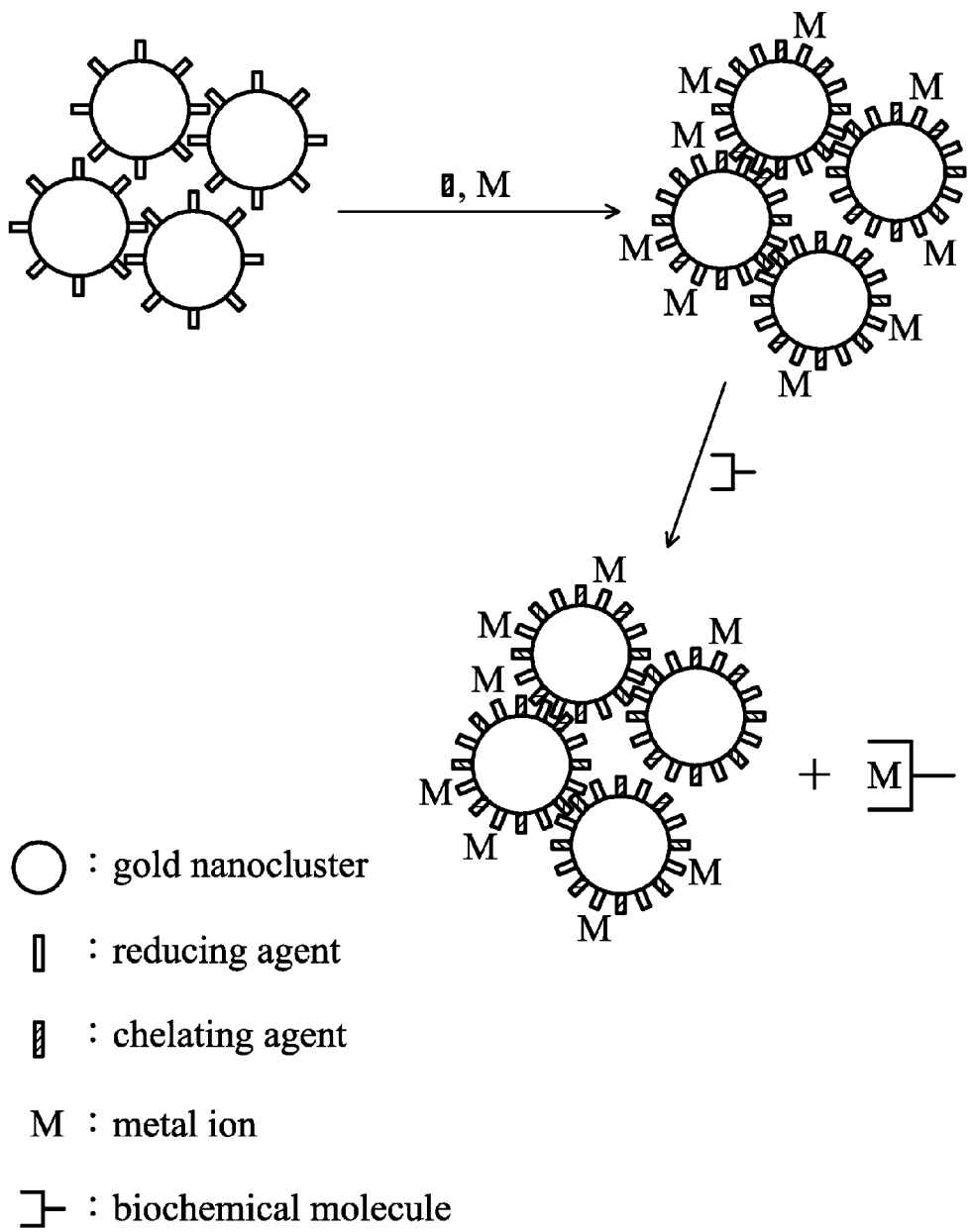
FIG. 2 shows a probe detecting chemical/biochemical molecules in one embodiment of the disclosure.
Figure 29:
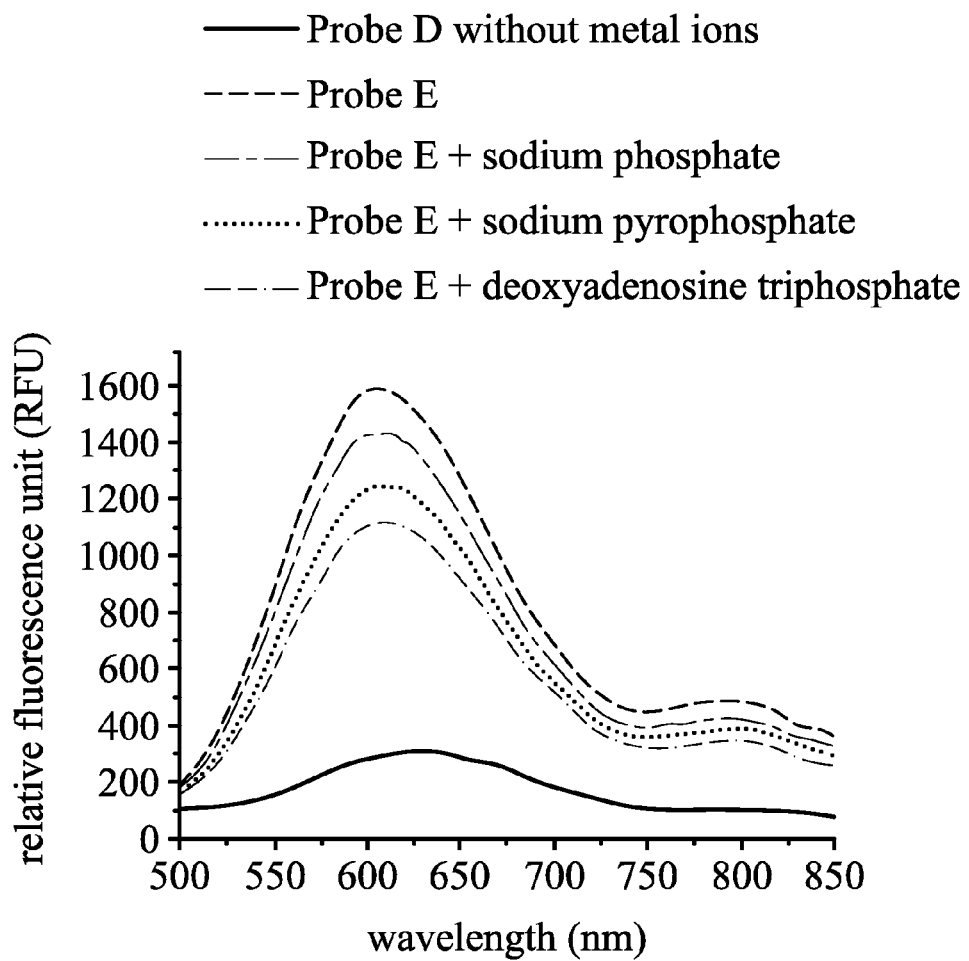
FIG. 29 shows a comparison of fluorescence spectra of Probe E before and after being mixed with chemical/biochemical molecules-containing solutions in one embodiment of the disclosure.

Probe E was mixed with 30 µL of solutions with different phosphate groups (10 µM) for 10 minutes to form respective mixtures. The fluorescence spectra of the mixtures are shown in FIG. 29. In the detection described above, sodium phosphate and sodium pyrophosphate served as chemical molecules, and deoxyadenosine triphosphate served as a biochemical molecule. As shown in FIG. 29, the interactions between the chemical/biochemical molecules with different phosphate groups and the $Gd^{3+}$ were different, thereby resulting in different changes of the fluorescence spectra. The mechanisms can be referred back to FIG. 2 the fluorescent gold nanoclusters with a surface capped by the reducing agent was mixed with the chelating agent (similar to the reducing agent) and the metal ions, such that the chelating agent were capped on the surface of the gold nanoclusters, and the metal ions were chelated to the chelating agent and the reducing agent. The biochemical/chemical molecules were mixed to the probe, thereby interacting with the metal ions on the surface of the probe.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A probe, comprising:
a gold nanocluster; and
glutathione partially capped on a surface of the gold nanocluster; and
N—[Nα,Nα-Bis(carboxymethyl)-L-lysine]-12-mercaptododecanamide partially capped on the surface of the gold nanocluster.

2. The probe as claimed in claim 1, wherein the probe is configured to detect $Co^{2+}$, $Ni^{2+}$, $Ag^+$, $Gd^{3+}$, $Al^{3+}$, $Zr^{4+}$, $Zn^{2+}$, $Fe^{3+}$, $Cd^{2+}$, $Ga^{3+}$, $Pb^{2+}$, $Eu^{3+}$, or $Cu^{2+}$.

3. A method for detecting metal ions, comprising:
providing a probe, wherein the probe includes:
a gold nanocluster;
glutathione partially capped on a surface of the gold nanocluster; and
N—[Nα,Nα-Bis(carboxymethyl)-L-lysine]-12-mercaptododecanamide partially capped on the surface of the gold nanocluster;
mixing the probe and an analyte solution to form a mixture, and analyzing the analyte solution to determine whether it contains specific metal ions or not, by comparing fluorescent spectra difference of the probe and the mixture.

4. The method as claimed in claim 3, wherein the metal ions comprise $Co^{2+}$, $Ni^{2+}$, $Ag^+$, $Gd^{3+}$, $Al^{3+}$, $Zr^{4+}$, $Zn^{2+}$, $Fe^{3+}$, $Cd^{2+}$, $Ga^{3+}$, $Pb^{2+}$, $Eu^{3+}$, or $Cu^{2+}$.

* * * * *